US012698315B2

(12) United States Patent
Cordes et al.

(10) Patent No.: US 12,698,315 B2
(45) Date of Patent: Aug. 4, 2026

(54) METHOD FOR TRANSDUCTION OF T CELLS IN THE PRESENCE OF MALIGNANT CELLS

(71) Applicant: MILTENYI BIOTEC B.V. & CO. KG, Bergisch Gladbach (DE)

(72) Inventors: Nicole Cordes, Bergisch Gladbach (DE); Thomas Schaser, Bergisch Gladbach (DE); Andrew Kaiser, Bergisch Gladbach (DE)

(73) Assignee: MILTENYI BIOTEC B.V. & CO. KG, Bergisch Gladbach (DE)

( * ) Notice: Subject to any disclaimer, the term of this patent is extended or adjusted under 35 U.S.C. 154(b) by 1169 days.

(21) Appl. No.: 17/642,188

(22) PCT Filed: Jul. 10, 2020

(86) PCT No.: PCT/EP2020/069484
§ 371 (c)(1),
(2) Date: Mar. 10, 2022

(87) PCT Pub. No.: WO2021/047804
PCT Pub. Date: Mar. 18, 2021

(65) Prior Publication Data
US 2022/0315894 A1 Oct. 6, 2022

(30) Foreign Application Priority Data

Sep. 11, 2019 (EP) ...................................... 19196735

(51) Int. Cl.
*C07K 14/725* (2006.01)
*A61K 40/11* (2025.01)
(Continued)

(52) U.S. Cl.
CPC .......... *C07K 14/7051* (2013.01); *A61K 40/11* (2025.01); *A61K 40/31* (2025.01);
(Continued)

(58) Field of Classification Search
CPC ................ C07K 14/7051; C07K 16/30; C07K 16/2896; C07K 2317/622; C07K 16/44;
(Continued)

(56) References Cited

U.S. PATENT DOCUMENTS

| | | | |
|---|---|---|---|
| 9,233,125 B2 | 1/2016 | Davila et al. | |
| 9,862,971 B2 | 1/2018 | Buchholz et al. | |
| 2008/0255004 A1 | 10/2008 | Neurauter et al. | |

FOREIGN PATENT DOCUMENTS

| | | |
|---|---|---|
| EP | 2725359 B1 | 5/2015 |
| EP | 3037821 A1 | 6/2016 |

(Continued)

OTHER PUBLICATIONS

Pfeiffer (Pfeiffer, Anett et al. "In vivo generation of human CD19-CAR T cells results in B-cell depletion and signs of cytokine release syndrome." EMBO molecular medicine vol. 10,11 (2018): e9158) (Year: 2018).*

(Continued)

*Primary Examiner* — Tracy Vivlemore
*Assistant Examiner* — Thomas R. Amick
(74) *Attorney, Agent, or Firm* — Kilpatrick Townsend & Stockton LLP

(57) ABSTRACT

The present invention provides an in-vitro method of reducing the efficiency of transducing malignant cells of the blood system of a subject that are not derived from T cells with lentiviral vector particles without reducing the efficiency of transducing T cells in a sample comprising T cells and said malignant cells. A combination of compositions comprising a first composition and a second composition is also disclosed, wherein said first composition comprises i) transduced T cells of a subject, wherein said transduced T cells express a CAR comprising an antigen binding domain, wherein the antigen binding domain of said CAR binds (Continued)

specifically to a tag of a tagged polypeptide, and ii) non-transduced malignant cells of the blood system of said subject, and wherein said second composition comprises said tagged polypeptide, wherein said tagged polypeptide binds specifically to an antigen expressed on the surface of said malignant cells. Alternatively, the transduced T cells of said first composition may comprise a nucleic acid encoding a CAR and an inducible gene expression system, and said second composition may comprise an induction agent inducing said gene system.

8 Claims, 5 Drawing Sheets

(51) Int. Cl.

| | |
|---|---|
| *A61K 40/31* | (2025.01) |
| *A61K 40/42* | (2025.01) |
| *C07K 14/705* | (2006.01) |
| *C07K 16/30* | (2006.01) |
| *C12N 5/0783* | (2010.01) |
| *C12N 15/62* | (2006.01) |
| *C12N 15/86* | (2006.01) |

(52) U.S. Cl.
CPC ...... *A61K 40/4211* (2025.01); *A61K 40/4224* (2025.01); *C07K 16/30* (2013.01); *C12N 5/0636* (2013.01); *C12N 15/625* (2013.01); *C12N 15/86* (2013.01); *C12N 2502/1107* (2013.01); *C12N 2740/15023* (2013.01); *C12N 2740/15042* (2013.01); *C12N 2830/002* (2013.01)

(58) Field of Classification Search
CPC ............... C07K 16/00; C07K 2319/03; C07K 2319/33; A61K 40/11; A61K 40/31; A61K 40/4211; A61K 40/4224; C12N 5/0636; C12N 15/625; C12N 15/86; C12N 2502/1107; C12N 2740/15023; C12N 2740/15042; C12N 2830/002; A61P 35/00
See application file for complete search history.

(56) References Cited

FOREIGN PATENT DOCUMENTS

| | | | |
|---|---|---|---|
| EP | 3336546 | A1 | 6/2018 |
| WO | 9631776 | A1 | 10/1996 |
| WO | 2012082841 | A2 | 6/2012 |
| WO | 2013044225 | A1 | 3/2013 |
| WO | 2013045639 | A1 | 4/2013 |
| WO | 2014127261 | A1 | 8/2014 |
| WO | 2015058018 | A1 | 4/2015 |
| WO | 2016030414 | A1 | 3/2016 |
| WO | 2016168766 | A1 | 10/2016 |
| WO | 2017091546 | A1 | 6/2017 |
| WO | 2019138217 | A1 | 7/2019 |
| WO | 2021047804 | A1 | 3/2021 |

OTHER PUBLICATIONS

Zhou (Zhou, Qi, et al. "T-cell receptor gene transfer exclusively to human CD8+ cells enhances tumor cell killing." Blood, The Journal of the American Society of Hematology 120.22 (2012): 4334-4342.) (Year: 2012).*

Levine BL, Miskin J, Wonnacott K, Keir C (2017) Global manufacturing of CAR T cell therapy. Mol Ther Methods Clin Dev 4: 92-101 (Year: 2017).*

Qasim W, Zhan H, Samarasinghe S, Adams S, Amrolia P, Stafford S, Butler K, Rivat C, Wright G, Somana K et al (2017) Molecular remission of infant B-ALL after infusion of universal TALEN gene-edited Car T cells. Sci Transl Med 9: 1-8 (Year: 2017).*

Koristka (Cartellieri, M., et al. "A Novel Ex Vivo Isolation and Expansion Procedure for Chimeric Antigen Receptor." (2014). (Year: 2014).*

Bender et al., Receptor-Targeted Nipah Virus Glycoproteins Improve Cell-Type Selective Gene Delivery and Reveal a Preference for Membrane-Proximal Cell Attachment, Public Library of Science Pathogens, vol. 12, No. 6, Jun. 9, 2016, pp. 1-28.

Cartellieri et al., Switching CAR T Cells On and Off: A Novel Modular Platform for Retargeting of T Cells to AML Blasts, Blood Cancer Journal, vol. 6, No. 8, Aug. 1, 2016, pp. 1-8.

Drent et al., Feasibility of Controlling CD38-CAR T Cell Activity with a Tet-on Inducible CAR Design, Public Library of Science ONE, vol. 13, No. 5, May 30, 2018, pp. 1-16.

Fesnak et al., Engineered T Cells: The Promise and Challenges of Cancer Immunotherapy, Nature Reviews Cancer, vol. 16, No. 9, Aug. 23, 2016, pp. 1-36.

Gu et al., Development of Inducible CD19-CAR T Cells with a Tet-On System for Controlled Activity and Enhanced Clinical Safety, International Journal of Molecular Sciences, vol. 19, No. 11, Nov. 3, 2018, pp. 1-12.

Holic et al., Influence of Mildly Acidic pH Conditions on the Production of Lentiviral and Retroviral Vectors, Human Gene Therapy Clinical Development, vol. 25, No. 3, Sep. 2014, pp. 1-24.

Jamali et al., Highly Efficient and Selective CAR-Gene Transfer Using CD4- and CD8-Targeted Lentiviral Vectors, Molecular Therapy: Methods & Clinical Development, vol. 13, Jun. 2019, pp. 371-379.

Lu et al., Preclinical Evaluation of Bispecific Adaptor Molecule Controlled Folate Receptor CAR-T Cell Therapy With Special Focus on Pediatric Malignancies, Frontiers in Oncology, vol. 9, Mar. 19, 2019, pp. 1-20.

Ma et al., Versatile Strategy for Controlling the Specificity and Activity of Engineered T Cells, Proceedings of the National Academy of Sciences of the United States of America, vol. 113, No. 4, Jan. 12, 2016, pp. E450-E458.

Ruella et al., Induction of Resistance to Chimeric Antigen Receptor T Cell Therapy by Transduction of a Single Leukemic B Cell, Nature Medicine, vol. 24, No. 10, Oct. 2018, pp. 1499-1503.

Sakemura et al., A Novel Strategy of Switching on/Off CD19CAR Expression Under Tetracycline-Based System, Blood, vol. 126, No. 23, Dec. 3, 2015, 4 pages.

Tokarew et al., Teaching an Old Dog New Tricks: Next-Generation CAR T Cells, British Journal of Cancer, vol. 120, No. 1, Nov. 9, 2018, pp. 26-37.

Zhang et al., A New Insight in Chimeric Antigen Receptor-engineered T Cells for Cancer Immunotherapy, Journal of Hematology & Oncology, vol. 10, No. 1, Jan. 3, 2017, pp. 1-11.

International Application No. PCT/EP2020/069484, International Search Report mailed on Sep. 18, 2020, 4 pages.

International Application No. PCT/EP2020/069484, International Preliminary Search Report, dated Mar. 15, 2024.

* cited by examiner

CD318-CAR= does not directly bind to malignant cells in the blood

CD318-CAR = does not directly bind
to malignant cells in the blood

Adapter-CAR = does not directly bind
to malignant cells in the blood

CD318-CAR = does not directly bind
to malignant cells in the blood

METHOD FOR TRANSDUCTION OF T CELLS IN THE PRESENCE OF MALIGNANT CELLS

FIELD OF INVENTION

The present invention relates to the field of CAR immunotherapy and reducing the efficiency of transducing non-target cells in a sample comprising target cells and non-target cells with lentiviral vector particles, in particular to the reduction of transducing malignant cells in a sample comprising T cells and malignant cells.

BACKGROUND OF THE INVENTION

Chimeric antigen receptor (CAR) T cell therapy has shown remarkable success for the treatment of a series of hematological malignancies such as acute lymphoblastic leukemia. It is based on genetically modifying T cells to express a tumor-specific CAR receptor that induces T cell activation, proliferation and cytolytic activity within the patient when the tumor antigen has been recognized. CARs specifically engage the target via the antigen recognition moiety, e.g. of a single chain variable fragment (scFV) derived from antibodies or a Fab fragment. The generation of gene-modified T cells is a complex process and typically starts with a heterogenous cell sample isolated from a patient such as from leukapheresis or peripheral blood mononuclear cells (PBMC). The heterogeneous cell sample may be either directly genetically modified or enriched first to yield the therapeutic relevant target cell type (i.e. T or NK cells) at purities above 90% to yield a more defined cell product which is then genetically modified.

The state of the art method for the genetic modification relies on the use of highly efficient gene delivery vehicles such as retroviral vectors that are established tools to correct defective genes and provide new functions to cells by inserting their therapeutic genetic cargo into the host cell genome. Retroviral vectors are enveloped particles that are typically pseudotyped with the membrane protein of the Vesicular Stomatitis Virus (VSV-G). For VSV-G, the envelope binds to the ubiquitously expressed Low-Density Lipoprotein Receptor (LDLR) such that a broad range of target cells may be transduced. Sufficient LDLR expression and transduction efficiency levels on T cells typically require polyclonal activation via CD3 and CD28. In contrast, on B cells engagement via CD40L in the presence of IL-4 or IL-21 is needed for activation. As alternative to VSV-G, the env protein of amphotropic murine leukaemia virus (4070A), the truncated envelope proteins of measles or Nipah virus or chimeric versions of envelope proteins derived from gibbon ape leukemia virus (GaLV) or feline endogenous retrovirus (RD114) have been used to pseudotype LVs.

Irrespective of the pseudotype used, the transduced T cells are then expanded in order to obtain sufficient cell numbers required for treatment, which are subsequently formulated and administered to the patient or cryopreserved and thawed before.

Lentiviral vectors (LV) are a subgroup of retroviral vectors, which are typically produced by transient transfection of HEK293T packaging cells. The LV membrane is derived from the packaging cells but host cell membrane proteins may be packaged as well—albeit at different levels based on the amino acid sequence of the transmembrane and cytoplasmatic domain. The most prominent membrane protein efficiently packaged into LV particles is CD63 with 4 transmembrane domains and short cytoplasmatic portions. CD9, another member of the tetraspanin family, is packaged as well and comprises are remarkably short cytoplasmatic tail. Long and/or bulky cytoplasmatic portions most likely interfere with HIV-1 matrix protein present on the inner side of the LV membrane, which may result in less efficient packaging into LV particle. This is supported by studies using heterologous membrane proteins as transduction markers (such as LNGFR) or fusogenic proteins used for pseudotyping to enable entry of the viral capsid in the cytoplasm of the target cells upon binding. VSV-G is an envelope protein that does not require engineering to enable efficient packaging. In contrast, alternative envelope proteins such as RD114, GALV and BaEV are only efficiently incorporated into the LV membrane when the cytoplasmic domain is replaced with the cytoplasmatic domain of Ampho-MLV env (4070A) which is 33 amino acids in total. The chimeric envelope proteins are termed RD114-TR, GALV-TR and BaEV-TR, respectively and provide new properties such as higher transduction efficiencies on the target cell type. For lentiviral vectors pseudotyped with measles virus envelope proteins truncation of the cytoplasmatic domain to up to 3 remaining acids for the MV-F fusion protein and up to 16 amino acids respectively for the MV-H hemagglutinin protein is required for the generation of functional lentiviral vectors.

CARs are typically composed of an extracellular antigen-recognition moiety that is linked, via spacer/hinge and transmembrane domains, to a cytoplasmatic signaling domain that can include costimulatory domains and T cell activation moieties. The cytoplasmatic portion of a $2^{nd}$ generation CAR provides stimulatory and costimulatory signal via two different domains derived from CD3zeta and CD137 respectively. The cytoplasmatic portion of a $2^{nd}$ generation CAR has in total more than 150 AA whereas $3^{rd}$ generation with an additional costimulatory domain derived from CD28 results in cytoplasmatic portion of in total more than 190 amino acids.

Recently, it has been reported that a truncated version of LNGFR with 8 remaining cytoplasmatic amino acids (dLNGFR) is efficiently incorporated into LV particles upon expression in the LV producer cells (Jamali et al, 2019). Upon incubation with target cells, dLNGFR was delivered as protein and was transiently detectable by flow cytometry on the target cells. In the same publication, experiments were conducted to determine whether CARs may be incorporated into LV particles as well. Although the viral supernatant was analyzed by multiple assays, only Western Blotting was able to detect CAR molecules in viral vector containing supernatant. In addition, no explanation on the mechanism nor any detail on the potential consequences was provided. Also the levels of CAR incorporation were not equally distributed for all analyzed types of pseudotyped LVs. In particular, for samples containing retargeted CD8 or CD4 specific LV CAR proteins was detectable. In contrast, for VSV-G pseudotyped LV the presence of CAR protein was not detectable or close to background levels although $3.54 \times 10E08$ particles were analyzed. Comparing the number of functional particles, an even higher number was applied for VSV-G pseudotyped LV supernatant as compared to the samples containing the alternative pseudotypes. Along the line, the authors speculate that the long cytoplasmic tail of the CAR comprising the 4-1BB and CD3zeta domains prevent efficient incorporation into LV particle. Even if low levels of CAR protein were detectable in the viral supernatant of transfected LV producer cells, the CAR protein is not necessarily incorporated into LV particles but more abundantly in non-functional LVs and extracellular vesicles such as microvesicles or exosomes. It is well known in the art that the number of total particles in LV containing supernatant is much higher than the number of functional LVs. In general, 1 in 100 to 1:1000 total particles are functional LVs particles.

The use of inducible systems to gain transcriptional control over CAR expression and therapeutic activity has been described in the art. E.g. Tet-on systems to induce CAR expression in the presence of supplemented Doxycyclin have shown efficacy in-vitro and in vivo (Drent et al., 2018 & Sakemura et al., 2015). After the removal of Doxycyclin, the CAR expression was diminished and cytolytic activity was reduced.

"Universal" CAR systems that indirectly bind to malignant target cells via soluble factors are described in the art. E.g. in WO2015058018A1 a CAR was engineered to be specific for the Fc portions of any immunoglobulin G antibody. In WO2012082841A2, WO2013044225A1 and WO2016030414A1 tagged antibodies and tag-specific CAR are disclosed, wherein the tag may be either artificial (such as FITC) and potentially immunogenic or an endogenous molecule which may compete with the natural counterparts to the CAR binding.

In clinical trials, antigen loss or downregulation by the malignant cells has been identified to be the most common cause of relapse for CAR T cell therapy. Thus, CAR constructs are currently under evaluation e.g. targeting antigens expressed at very low levels or by targeting multiple antigens simultaneously. Related to antigen escape, a rare type of relapse has been recently reported upon treating a B cell ALL patient with anti-CD19 CAR T cells, when malignant B cells were unintentionally genetically modified during CAR T cell manufacturing (Ruella M et al., 2018). In this clinical trial, the leukapheresis product was activated with CD3 and CD28 specific antibodies coupled to beads without prior T cell isolation and subsequently transduced with CD19 CAR encoding LV. For CTL019, the mean leukemia burden in the apheresis product was 25% (n=117; adult and pediatric ALL patients). T cells but also residual malignant B cells were transduced with CD19 CAR encoding lentiviral vector and the CAR was expressed on both cell types. Expression of the CD19-CAR in cis on the malignant cell resulted in masking of the CAR target epitope and thereby to CAR resistance and loss of therapeutic efficacy. The authors confirmed that the relapsed malignant B cell population originated from one single malignant B cell.

While it is easier and less expensive to generate CAR T cells directly by transduction of PBMC or leukaperesis products, it theoretically creates a less defined cell product and increases the risk of carryover of malignant cells and thereby the described effect of transduction of malignant cells. Enrichment of T cell prior to transduction decreases the amount of malignant cells strongly.

WO2019138217A1 discloses a method of transducing a sample composed of two cell populations with CAR encoding lentiviral vectors wherein one cell population expresses the antigen of the CAR and the other cell population does not express the antigen of the CAR. A specific range of LV dose per cell was defined as multiplicity of infection (MOI) inducing transduction of the target cell population to a greater extent than the transduction of the non-target cell population. However, there is no international standard to quantify LVs, thus there is also no clear definition of MOI. A wide variety of protocols for research grade but also for clinical grade LVs are available to quantify LVs based on function but different experimental settings typically result in a more than ten-fold change even though the same LV sample may have been analyzed. In addition, in WO2019138217A1 the MOI was selected to be sufficiently low to induce acceptable transduction efficiency levels on the target cell population while the transduction efficiency on the non-target cell population was close to detection levels. However, this setting excludes applying high LV doses, which might be necessary for specific therapeutic applications, when low transduction efficiencies exert no or little therapeutic effect. Moreover, even after adjusting the LV dose to theoretical or historical specifications, the resulting transduction efficiency on the actual cell sample may not match. This is mainly because the prediction of the transduction efficiency on primary material such as T cells is difficult as variations between material derived from different healthy donors and even more pronounced between material of different patients are typically observed. To avoid such variations in a clinical setting, specifications on minimum transduction efficiency levels are only met by applying high MOIs.

Thus, there is a need in the art for improved and/or alternative methods reducing the efficiency of transducing malignant cells with a lentiviral vector particle without reducing the efficiency of transducing T cells in a sample comprising malignant cells and T cells.

SUMMARY OF THE INVENTION

It was found that lentiviral vector particles comprising a nucleic acid encoding a CAR also display said CAR on the membrane of the lentiviral vector particle. In case the CAR comprises an antigen binding domain that is specific for an antigen expressed on a malignant cell such as a malignant B cell, said lentiviral vector particle will bind to said malignant cell. This is an unwanted result in a process of transducing T cells, wherein in the sample is a mixed cell population also comprising malignant cells.

As described above WO2019138217 discloses a specific LV dose to increase the transduction efficiency on the target cell population not expressing the CAR antigen and to reduce the transduction efficiency on the non-target cell population expressing the CAR antigen.

It was unexpected that it is possible to have innocuously or at least less innocuously the same malignant cells in a cell sample to be transduced with a lentiviral vector particle that allows to use the transduced cells of said sample in the treatment of a cancer in a subject, wherein said cancer is caused by the same malignant cells that are in said sample, when the lentiviral vector particle has a configuration as disclosed herein. This is due to the reduction of efficiency of transducing malignant cells in a sample comprising T cells and malignant cells but without reducing the efficiency of transducing T cells in said sample. Key is here the configuration of the lentiviral vector particle that is used for transduction of the cells of said sample. Said configuration of the lentiviral vector particle may allow for lentiviral vector particle transduction into target cells independently of concentrations used of said lentiviral vector particle.

Lentiviral vector particles encoding a CAR specific for a tag of a tagged polypeptide have a broad tropism due the viral envelope protein used for pseudotyping. This includes also T cells and malignant cells but the lentiviral vector particle has no specificity for the tumor antigen expressed on said malignant cells by said CAR displayed on the surface of said lentiviral vector particle. T cells transduced by said lentiviral vector particles nonetheless induce indirectly specific lysis of said malignant cells in a CAR T cell therapy by using specificity against exactly said tumor antigen, wherein the transduced T cells express an antigen binding domain that is specific for a tag, wherein the binding to said tumor antigen is via a tagged polypeptide (or adapter) that is bound by the antigen binding domain of the CAR and binds itself to the tumor antigen. Therefore, binding to any human target cell requires the presence of an adapter molecule that is not present during the transduction. The indirect system is also referred to as "Adapter-CAR" system.

In addition surprisingly, the inventors of the present application found out that the inadvertent transduction of the malignant cells such as malignant B cells expressing the antigen of the transduced CAR can be inhibited or at least reduced in a LV particle dose independent manner by using lentiviral vector constructs that do not display the CAR on the surface of the lentiviral vector particle. This can be achieved by using gene expression systems for expression of said CAR in the T cells, such as using inducible gene expression systems.

The concept has been shown exemplary using anti-CD19 CAR known to be able to bind to (malignant) B cells and CAR constructs known to be not able to bind to (malignant) B cells (CD318-CAR or Adapter-CAR). All types of CAR are displayed and presented on the LV surface to cells in a sample that may comprise T cells and malignant B cells. These findings provide multiple solutions that may reduce the risk of transducing malignant B cells, subsequent antigen loss/masking and relapse as disclosed herein.

The present invention exploits this finding by providing methods for the reduction of efficiency of transducing unwanted malignant cells without reducing the efficiency of transducing T cells using lentiviral vector particles encoding for a CAR, wherein the antigen binding domain directly (via said gene expression system) or indirectly (via said adapter CAR system) bind to the antigen expressed on said malignant cell. Herein a combination of compositions is also disclosed, wherein a first composition comprises transduced T cells expressing said CAR that binds to a tag and malignant cells as disclosed herein, and the second composition comprises a tagged polypeptide that allows the CAR of the transduced T cells of the first composition to bind to said antigen expressed on the surface of said malignant cells. Alternatively, said first composition comprises transduced T cells expressing said CAR by induction as disclosed herein that binds to said antigen expressed on the surface of said malignant cells and said malignant cells as disclosed herein, and the second composition comprises an induction agent that allows the CAR to be expressed on the surface of said transduced T cells.

Figure 1:
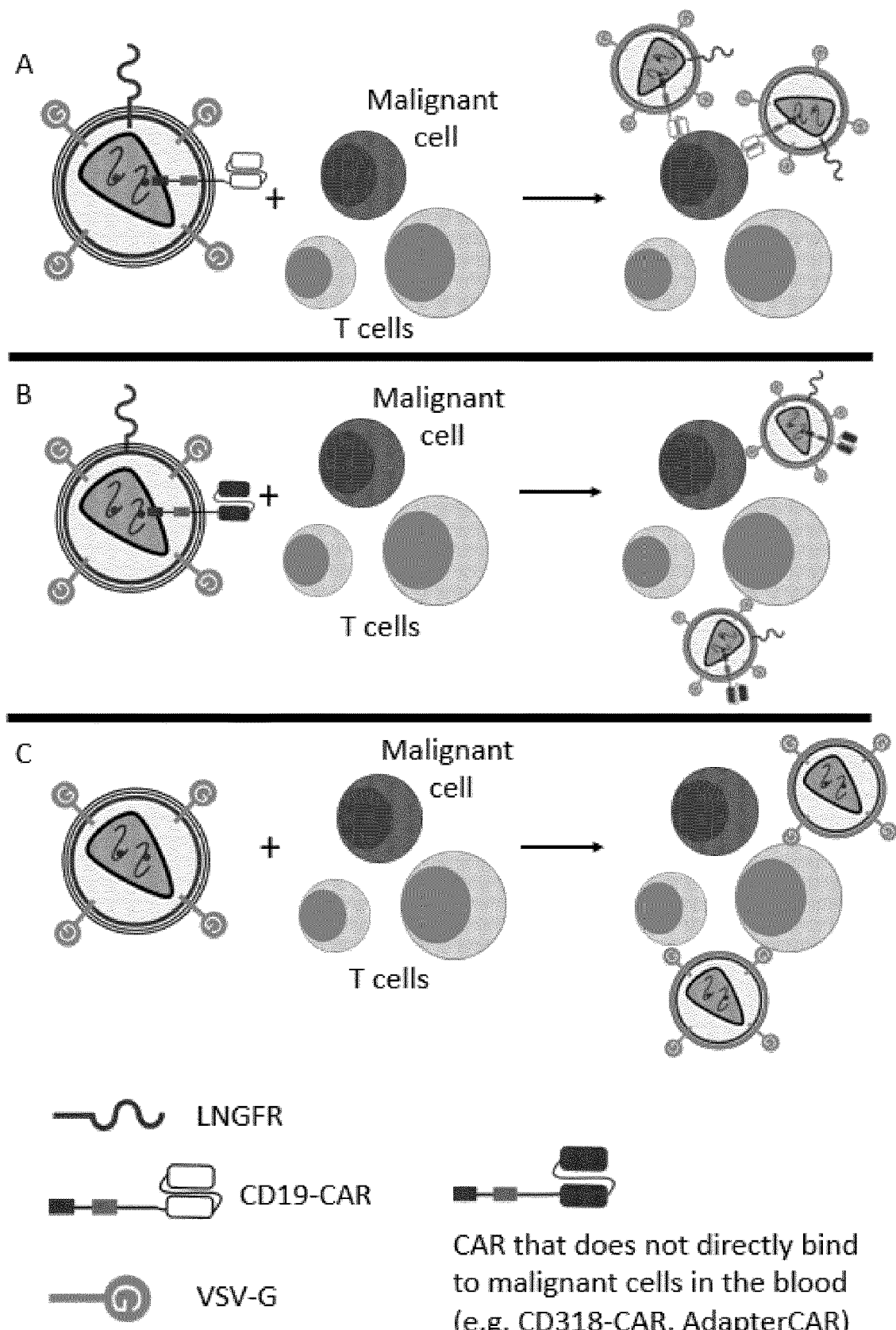
FIG. 1: Overview of how the technology of this disclosure can be used to make CAR-T cells in situ using a mixed sample of peripheral blood mononuclear cells (PBMC) from a cancer patient who has a blood cell malignancy. The technology considerably facilitates production of the CAR-T cells by eliminating the requirement that the PBMC be enriched for T cells before transfection.

Panel A shows the previous state of the art for making CAR-T cells. On the left side is a lentiviral vector particle with a gene that encodes a chimeric antigen receptor (CAR) (white) that is specific for a target antigen on a circulating malignant cell (CD19). The vector may also bear a peptide tag (LNGFR) for following transduction. A mixed PBMC population directly obtained from the patient (as depicted here) cannot be used efficiently as the source of the T cells.

The vector encoding the CAR is diverted away from the T cells by malignant cells in the population that bear CD19 (right). This is because the vector doesn't just encode the CAR: it also displays the CAR on its surface, placed there by the HEK vector packaging cell. Because the malignant cells in the PBMC sample express CD19, an inadequate number of therapeutic CAR-T cells are produced, contaminated with bystander malignant cells that have been genetically modified.

Panel B shows how a lentiviral vector particle can be reconfigured in accordance with this invention for transforming T cells in a PBMC sample without purifying the T cells. More CAR-T cells and fewer modified malignant cells are produced. Here, the CAR is an AdapterCAR (black) that doesn't bind CD19 directly. Instead, it is specific for a tagged polypeptide, which in turn is specific for CD19. The lentiviral vector expresses on its surface both the Adapter-CAR and G protein from vesicular stomatitis virus (VSV G), which binds preferentially to the LDL receptor on T cells. When combined with a PBMC population from the patient, the vector will not be diverted by malignant cells, because the CAR does not bind CD19. Instead, the vector transduces T cells specifically, transfecting via the LDL receptor. In therapy, the CAR-T cells are administered to the patient in combination with the tagged polypeptide, which adapts the CAR-T cells to bind and remove the CD19 positive malignant cells in vivo.

Panel C shows another way a lentiviral vector particle can be reconfigured in accordance with this invention for transforming T cells in a PBMC sample without purifying the T cells. Here, the CAR is specific for CD19, as in Panel A. Here, the lentiviral vector encodes the CAR, but does not display the CAR on its surface, because the CAR encoding region in the packaging cells is placed under control of an inducible or tissue specific promoter. When combined with a PBMC sample from the patient, the vector transduces T cells by by way of the LDL receptor, and is not diverted by CD19 positive malignant cells. In therapy, if an inducible promoter is used, the CAR-T cells are administered to the patient in combination an induction agent for the promoter. This causes the CAR to be expressed on the CAR-T cells, so that the CAR-T cells can bind and remove the CD19 positive malignant cells in vivo. If a tissue specific promoter is used instead, expression of the CAR is automatically turned on once the CAR encoding sequence is delivered into the T cells. An induction agent is not needed.

Figure 2A:
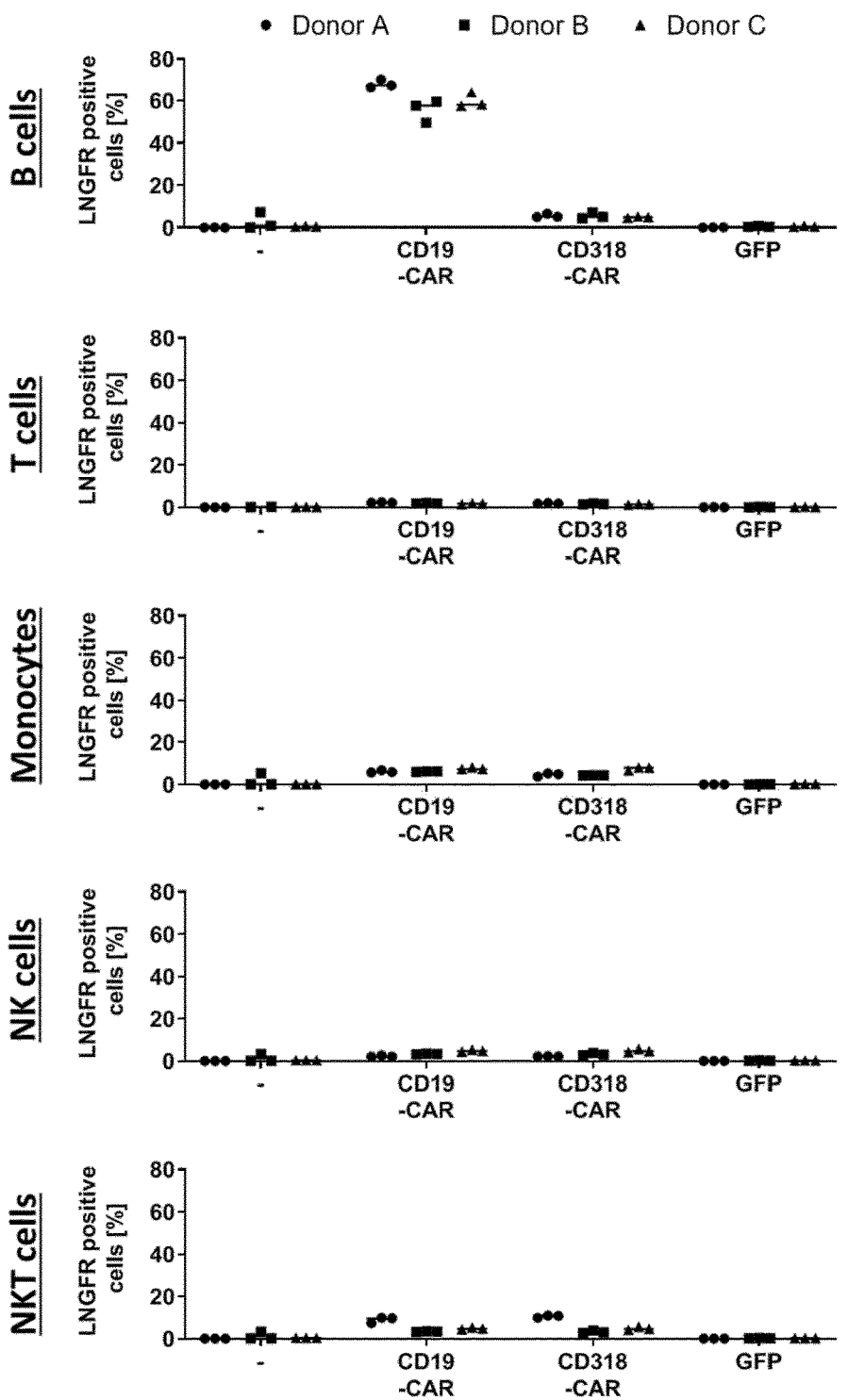

FIG. 2: Binding of lentiviral vector particles via the displayed CAR to PBMC.

A Freshly isolated unstimulated PBMC were left untreated (-) or were incubated with the same dose of VSV-G pseudotyped lentiviral vector particles encoding for and displaying CD19-CAR or CD318-CAR for 1 h at 4° C. LNGFR that is displayed on the surface of lentiviral vector particles was used as marker for the detection of bound lentiviral vector particles to the different cell types as quantified by flow cytometry by LNGFR staining. As control, the same dose of GFP encoding lentiviral vector particles was used and the binding to the different cell types was quantified by flow cytometry.

B Freshly isolated unstimulated PBMC were treated with a CD19-antibody in increasing concentrations (0 ng/ml to 5000 ng/ml) for 30 min at 4° C. to block the CD19 epitope recognized by the CD19 specific CAR. The same dose of lentiviral vector particles pseudotyped with VSV-G displaying either CD19-CAR or CD318-CAR was applied. As control, untreated cells (w/o) or cells incubated with the same dose of GFP encoding lentiviral vector particles was used. The presence of lentiviral vector particles on B cells was analyzed by flow cytometry by quantifying the ratio LNGFR positive cells.

Figure 3:
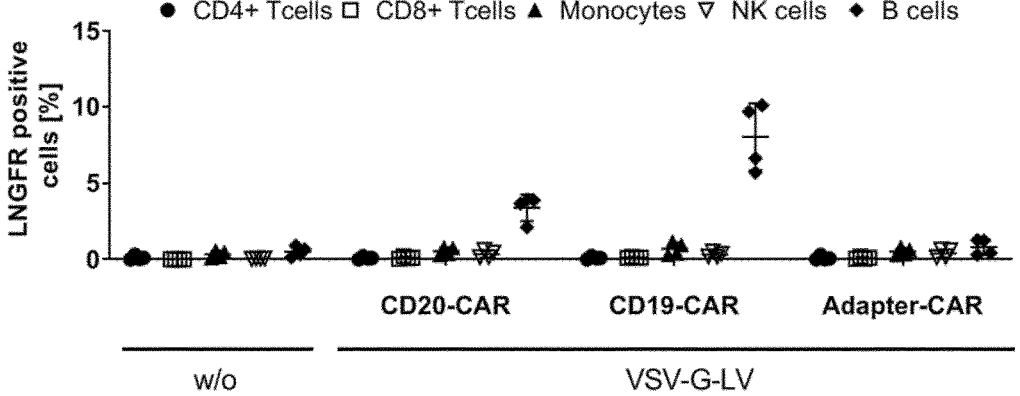

FIG. 3: Binding of lentiviral vector particles displaying direct CARs or AdapterCAR. Freshly isolated unstimulated PBMC were either left untreated (w/o) or were incubated with the same dose of VSV-G pseudotyped lentiviral vector particles encoding for and displaying CD19-CAR, CD20-CAR or Adapter-CAR for 1 h at 4° C. and the binding of lentiviral vector particles to the different cell types was quantified by flow cytometry by quantifying the ratio of LNGFR positive cells.

Figure 4:
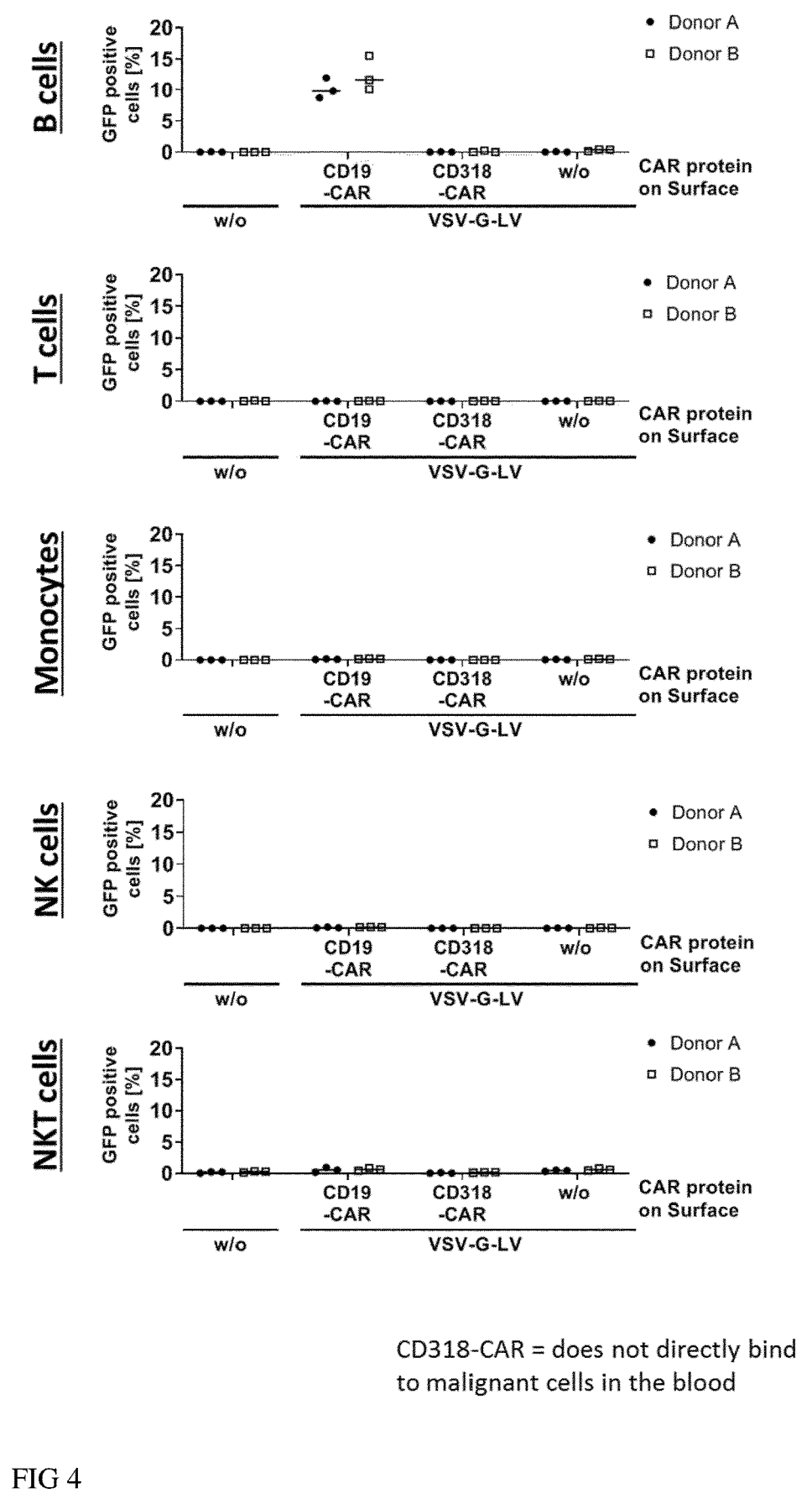

FIG. 4: Binding of GFP encoding lentiviral vector particles delivering also GFP as protein and displaying different CAR constructs.

Lentiviral vectors displaying different CAR constructs but encoding for and delivering the same marker protein (GFP) were generated to facilitate a better comparison of the different CAR constructs using the same way of detection and sensitivity. Freshly isolated unstimulated PBMC were incubated with GFP encoding VSV-G pseudotyped lentiviral vector particles delivering also GFP as protein and displaying either CD19-CAR or CD318-CAR. As control, untreated PBMC (w/o) or PBMC incubated with GFP encoding VSV-G pseudotyped lentiviral vector particles delivering also GFP as protein but without displayed CAR were analyzed. The binding of the different types of lentiviral vectors particles on the different cell types was quantified as the ratio of GFP positive cells analyzed by flow cytometry.

Figure 5:
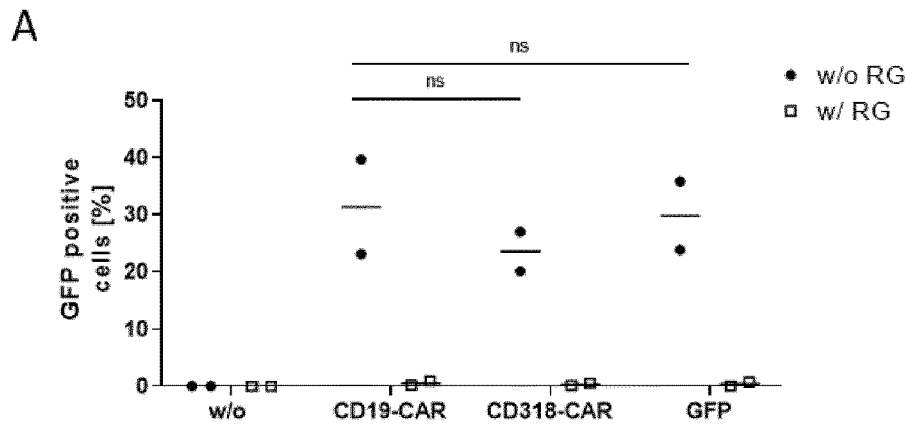
Figure 5:
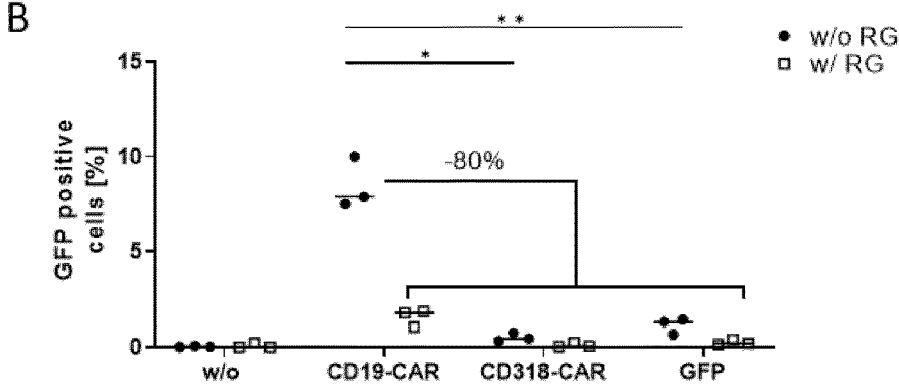
Figure 5:
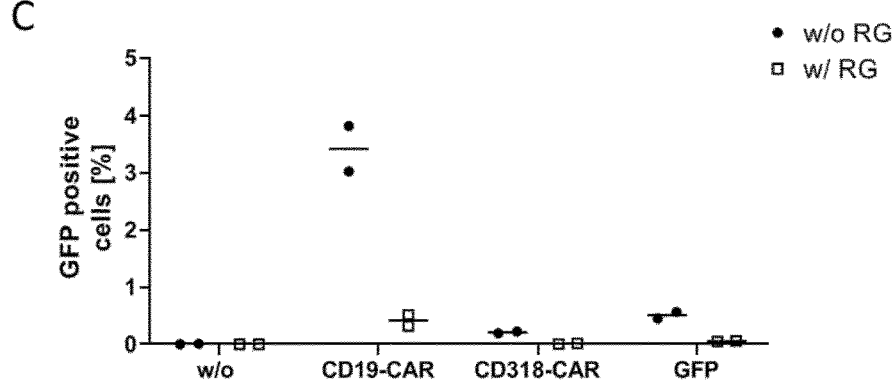

FIG. 5: Transduction of mixed cell populations comprising T cells and malignant cells with lentiviral vectors encoding for GFP and displaying the different CAR constructs.

A Initially, isolated and activated T cells were transduced without added malignant cells under standard conditions with lentiviral vector constructs displaying different CAR constructs to confirm the results of the LV titration and that the same LV dose was applied. Therefore, T cells of two healthy donors were isolated from PBMC and activated overnight via CD3 and CD28. Half of the samples were incubated for 30 min with the integration inhibitor Raltegravir (w/RG) or left untreated (w/o RG) to identify false positive results from protein transfer (i.e. pseudotransduction). As control, the T cells were subsequently incubated with VSV-G pseudotyped lentiviral vector particles encoding for GFP but displaying either CD19-CAR, CD318-CAR or no CAR (w/o) within the envelope of the lentiviral vector particles. Three days post activation the medium of the cells was exchanged with fresh cultivation medium in order to remove the transact. The transduction efficiency was analyzed 4 d post transduction by quantification of the GFP positive T cells by flow cytometry.

B PBMC of a healthy donor were isolated from Buffy Coat and mixed with 30% malignant B cells of three different B-ALL patients. Half of the samples were incubated for 30 min with the integration inhibitor Raltegravir (w/RG) or left untreated (w/o RG) to identify false positive results from protein transfer (i.e. pseudotransduction). As control, the coculture of PBMC and malignant B cells was left untreated (w/o) or incubated with VSV-G pseudotyped lentiviral vector particles encoding for GFP but displaying either CD19-CAR, CD318-CAR or no CAR (w/o) within their envelope. After binding for 1.5 h at 37° C. unbound lentiviral vector particles were removed by extensive washing. Transduction was analyzed 4 d post incubation by quantification of the GFP positive malignant B cells by flow cytometry.

C Isolated T cells of two healthy donors were activated overnight via CD3 and CD28 specific antibodies. The activated T cells were mixed with 30% malignant B cells of one B-ALL patient. Half of the samples were incubated for 30 min with the integration inhibitor Raltegravir (w/RG) or left untreated (w/o RG) to identify false positive results from protein transfer (i.e. pseudotransduction). As control, the co-culture was left untreated (w/o) or was incubated with VSV-G pseudotyped lentiviral vector particles encoding for GFP but displaying either CD19-CAR, CD318-CAR or no CAR (w/o) within the envelope of the lentiviral vector particles. After binding for 1.5 h at 37° C. excess lentiviral vector particles were removed by extensive washing. Transduction was analyzed 4 d post transduction by quantification of the GFP positive malignant B cells by flow cytometry.

DETAILED DESCRIPTION OF THE INVENTION

The present invention provides methods for the generation of CAR expressing T cells (CAR T cells) with lentiviral vector particles in a sample comprising T cells and malignant cells.

In a first aspect, the present invention provides an in-vitro method of reducing the efficiency of transducing malignant cells of the blood system of a subject that are not derived from T cells with lentiviral vector particles without reducing the efficiency of transducing T cells in a sample comprising T cells and said malignant cells, wherein said lentiviral vector particles are pseudotyped with an envelope protein selected from the group consisting of BaEV env, VSV-G, RD114-TR, GALV-TR, MV-H/F, NiV-G/F, and Ampho-MLV env, and wherein said lentiviral vector particles comprise a nucleic acid encoding a chimeric antigen receptor (CAR) comprising an antigen binding domain, wherein said antigen binding domain of said CAR specifically binds to a tag of a tagged polypeptide, wherein said polypeptide specifically binds to an antigen expressed on the surface of said malignant cells, the method comprising a) providing said sample comprising T cells and said malignant cells b) Incubation of the cells of said sample with said lentiviral vector particles, thereby generating a sample comprising transduced T cells, wherein the efficiency of transducing said malignant cells induced by said incubation is reduced compared to the efficiency of transducing said malignant cells of said sample comprising T cells and said malignant cells wherein/when said lentiviral vector particles are replaced by lentiviral vector particles comprising a nucleic acid encoding a CAR comprising an antigen binding domain, wherein said CAR has an antigen binding domain specific for an antigen that is expressed on the surface of said malignant cells, thereby generating lentiviral vector particles comprising said CAR that has an antigen binding domain specific for an antigen that is expressed on the surface of said malignant cells.

Due to the envelope protein said lentiviral particle has a broad tropism comprising T cells and said malignant cells of the blood system of a subject that are not derived from T cells.

Due to the display of a CAR on the surface of the lentiviral vector particle that is specific for said antigen expressed on the surface of said malignant cells said lentiviral vector particle that is used as reference has a specificity for said malignant cell.

Said method, wherein said method comprises the steps a) providing said sample comprising T cells and said malignant cells b) Incubation of the cells of said sample with said lentiviral vector particles, wherein said method is performed in equal or less than 144 hours, less than 120 hours, less than 96 hours, less than 72 hours, less than 48 hours, or less than 24 hours.

Said method, wherein said antigen expressed on the surface of said malignant cells is a tumor associated antigen (TAA).

Said method, wherein said sample comprising T cells and said malignant cells are provided by a subject suffering from a malignancy caused by said malignant cells in said subject's blood system that are not derived from T cells.

Said method, wherein said reduced efficiency of transduction of said malignant cells is due to the lack of the presence of said CAR that has an antigen binding domain specific for an antigen that is expressed on the surface of said malignant cells on the surface of the lentiviral vector particle.

Said method, wherein said efficiency of transducing said malignant cells is reduced for at least 30%, for at least 40%, for at least 50%, for at least 60%, for at least 70%, for at least 80%, for at least 90%, for at least 95%.

Said method, wherein said method comprises step c) removal of residual lentiviral vector particles. Said removal of residual lentiviral vector particles may be performed by washing, wherein the washing results in an at least 10-fold, at least 100-fold, preferably at least 1000-fold reduction of residual vector particles in the sample that comprises the genetically modified T cells, i.e. transduced T cells.

The washing step may be performed by a series of media/buffer exchanges (at least twice exchanges) thereby removing said residual lentiviral vector particles from said sample comprising said genetically modified T cells. The exchanges may be performed by separation of cells and media/buffer by centrifugation, sedimentation, adherence or filtration and subsequent exchange of media/buffer.

The at least 10-fold, at least 100-fold, preferably at least 1000-fold reduction of residual vector particles in the sample that comprises the genetically modified T cells by washing can be achieved for example by i) Separating cells and media/buffer ii) Removal of 90%, 99%. preferably 99,9% of the volume of media/buffer iii) Adding new media/buffer to the original volume.

iv) Resuspension of cells in media/buffer

Washing steps may be performed in a consecutive manner that may result in a cumulative reduction of lentiviral vectors (i.e. two washing steps with a 10-fold reduction per step result in cumulative reduction of 100-fold).

Said removal of residual lentiviral vector particles may be performed by incubation with substances that inactivate lentiviral vector particles and/or reduce their stability. Substances that inactivate lentiviral vector particles and/or reduce their stability may be washed away after said incubation, wherein said incubation occurs for no longer than 3 hours, preferentially no longer than 1 hour. Such substances that inactivate lentiviral vector particles and/or reduce their stability may be e.g. Heparin, antiretrovirals, complement factors of a human blood, neutralizing antibodies that a contained in human blood or a mild basic buffer.

Said antiretrovirals may be e.g. inhibitors of viral enzymes such as Zidovudin (zidothymidin, AZT) or Raltegravir.

Complement factors and/or neutralizing antibodies that are contained in blood, e.g. human blood, may be isolated by methods well-known in the art.

The mild basic buffer may have a pH value of about 7 to 9, being sufficiently mild to not harm the T cells of the sample. Such a buffer is described e.g in Holic et al. (2014)

Said CAR may comprise an antigen binding domain, a transmembrane domain and an intracellular signaling domain as described herein.

Said method, wherein said wherein said lentiviral vector particles that comprise a nucleic acid encoding a chimeric antigen receptor (CAR) as disclosed herein do not comprise a further nucleic acid encoding a CAR comprising an antigen binding domain specific for an antigen expressed on the surface of said malignant cells.

Said sample comprising T cells and said malignant cells may be whole blood of a subject, a leukapheresis, buffy coat, PBMC, outgrown or isolated T cells. Preferentially the cells of said sample are human cells.

Said malignant cells of the blood system of a subject that are not derived from T cells may cause a malignancy in said subject.

Said method, wherein said malignant cells of the blood system of a subject that are not derived from T cells may be circulating tumor cells (CTC), malignant B cells, malignant B cell subsets, malignant B cell progenitors, malignant NK cells, malignant stem cells, malignant myeloid cells, malignant myeloid subset or malignant myeloid progenitor cells.

Said malignant B cells may cause a B cell malignancy in said subject selected from the group, consisting of B-ALL, pre-pre-B ALL (pro-B-ALL), pre-B ALL, mature B-cell ALL, B cell lymphoma and B-CLL.

Said malignant myeloid cells may cause a myeloid malignancy selected from the group consisting of acute myeloid leukemia (AML), acute myeloblastic leukemia, acute promyelocytic leukemia, acute myelomonocytic leukemia, acute monoblastic leukemia, acute monocytic leukemia, acute erythroid leukemia and acute megakaryoblastic leukemia.

Said method, wherein the transduced T cells may express said CAR and said transduced T cells may be for use in treatment of said subject suffering from a malignancy caused by said malignant cells. Said transduced T cells or said sample comprising said transduced T cells may be suited for use in treatment of said subject suffering from a malignancy caused by said malignant T cells, when both said transduced T cells (or said sample comprising said transduced T cells) and said tagged polypeptide may be administered to said subject.

Said method wherein said transduced T cells that may express said CAR may indirectly bind to an antigen expressed on the surface of said malignant cells via said tagged polypeptide, when said transduced T cells and said tagged polypeptide may be administered to said subject.

Said method, wherein said transduced T cells of said sample expressing said CAR may be for use in treatment of a malignancy caused by said malignant cells in said subject, wherein the antigen binding domain of said CAR indirectly may bind to the antigen expressed on the surface of said malignant cells in said subject via the tagged polypeptide that may bind to the antigen on the surface of the malignant cells after administration of said transduced T cell expressing said CAR (or said sample comprising said transduced T cells) together simultaneously or subsequently with said tagged polypeptide.

Said method, wherein said sample comprising said transduced T cells may be for use in a method of treating a malignancy caused by said malignant cells in said subject, the method comprising i) administering to said subject said sample comprising said transduced T cells, and ii) administering said tagged polypeptide to said subject.

If said administration of said sample comprising said transduced T cell expressing the CAR and said administration of said tagged polypeptide may be performed subsequently, the transduced T cell expressing the CAR may be applied first to the subject before administration of said tagged polypeptide, or said tagged polypeptide may be applied first to the subject before administration of said transduced T cell expressing said CAR.

Alternatively, said administrations of said sample comprising said transduced T cell expressing the CAR and of said tagged polypeptide may be performed simultaneously.

Preferentially said lentiviral vector particle is pseudo-typed with VSV-G.

Said method, wherein said tag of said tagged polypeptide is a molecule that is present at low levels on the cell surface, preferentially it is not naturally present on the cell membrane (cell surface) of human blood cells.

Said method, wherein said antigen binding domain of the CAR binds to a tag selected from the group consisting of dextran, biotin, fluorescein isothiocyanate (FITC), phyco-erythrin (PE), peptides such as c-Myc-tag, Strep-Tag, Flag-Tag, Polyhistidine-tag or proteins such as streptavidin. Preferentially, the tag may be biotin or a derivate thereof.

Said method, wherein said subject may be a human.

Said method, wherein said antigen binding domain of the CAR may be a scFv.

Said method, wherein said polypeptide that binds to an antigen expressed on the surface of said malignant cells may be or may comprise an antibody or antigen binding fragment thereof.

Said method, wherein the MOI during the incubation is higher than 1, higher than 5, higher than 10, higher than 20, higher than 50, higher than 100.

Said method, wherein said malignant cells of the blood system of a subject may be malignant B cells, malignant B cell subsets or malignant B cell progenitors and said antigen that may be expressed on the surface of said malignant cells may be selected from the group consisting of CD5, CD10, CD15, CD19, CD20, CD22, CD24, CD30, CD33, CD34, CD38, CD70, CD79a, CD123.

Preferentially said antigen may be CD19.

Said method, wherein the T cells of said sample comprising T cells and said malignant cells may be activated T cells.

Said method, wherein the T cells of said sample comprising T cells and said malignant cells may be non-activated T cells.

Said method, wherein said T cells of said sample may be activated by modulatory agents before said incubation.

Said method, wherein said T cells of said sample may be activated by modulatory agents during said incubation.

Said method, wherein said T cells of said sample are not activated by modulatory agents.

Said method, wherein said T cells of said sample may activated by said malignant cells Said method, wherein said modulatory activating agents may be removed after the addition of said modulatory agents to the T cells.

Said method, wherein said modulatory activating agents may be removed in less than 2 hours, preferentially in less than 1 hour, more preferentially in less than 30 minutes after the addition of said modulatory agents to the T cells.

Said method, wherein said modulatory agents comprise an antibody or antigen binding fragment thereof specific for CD3 and/or an antibody or antigen binding fragment thereof specific for CD28 coupled directly or indirectly via a linker, wherein said antibodies or antigen binding fragments thereof specific for CD3 and CD28 can be removed.

Said removal of the modulatory agents from the cells may be further performed by one or more washing steps.

Said method, wherein said modulatory agents comprise an antibody or antigen binding fragment thereof specific for CD3 and/or an antibody or antigen binding fragment thereof specific for CD28 coupled directly or indirectly via a linker, wherein said antibodies or antigen binding fragments thereof specific for CD3 and CD28 can be disrupted chemically and/or enzymatically, and wherein said modulatory agents are removed by chemical and/or enzymatical disruption of said antibodies or antigen binding fragments thereof specific for CD3 and CD28. Removal of the disrupted modulatory agents from the cells may be further performed by one or more washing steps.

The methods and systems described herein for removal of magnetic particles from a cell that have been directly or indirectly bound to said cell may also be suitable, may be transferred to and/or may be applied for the removal of said modulatory agents that comprise an antibody or antigen binding fragment thereof specific for CD3 and an antibody or antigen binding fragment thereof specific for CD28 coupled directly or indirectly via a linker.

Said method, wherein said removal of said modulatory agents of said antibodies or antigen binding fragments thereof specific for CD3 and/or CD28 is performed by a) a competitive reaction comprising the step of adding a competing agent that competes with a tag, e.g. biotin (as a competitor), if said modulatory agents comprise indirectly coupled antibodies or antigen binding fragments thereof, such as Fabs, specific for CD3 and/or CD28 via two components, wherein said two components may be i) antibodies or antigen binding fragments thereof, such as Fabs, specific for CD3 and/or CD28 are coupled to said tag such as PEO-Biotin, or antibodies or antigen binding fragments thereof, such as Fabs, specific for CD3 and/or CD28 that are coupled via a linker such as dextran that is coupled to said tag such as PEO-biotin, and ii) antibodies or antigen binding fragments thereof, such as Fabs, specific for the tag, e.g. biotin, and wherein said to components i) and ii) have been combined and contacted with said cells, and/or b) an enzymatic disruption comprising the step of adding an enzyme that biodegrades said linker, if the linker is a biodegradable linker (i.e. an indirect or direct linkage of the two antibodies or antigen binding fragments thereof via the linker).

In another preferred embodiment of the invention, said modulatory agents comprise indirectly coupled antibodies or antigen binding fragments thereof, such as Fabs, specific for CD3 and/or CD28 via two components:

i) antibodies or antigen binding fragments thereof, such as Fabs, specific for CD3 and/or CD28 are coupled to a tag such as PEO-Biotin, or antibodies or antigen binding fragments thereof, such as Fabs, specific for CD3 and/or CD28 that are coupled via a linker such as dextran that is coupled to a tag such as PEO-biotin ii) antibodies or antigen binding fragments thereof, such as Fabs, specific for the tag, e.g. biotin, wherein after combining component I and ii and after contacting the T cells with said combined components, said combined components may be disrupted (removed) by adding a competing agent that competes with said tag, e.g. biotin (as a competitor).

Said biodegradable linker may be or may comprise a polysaccharide and said enzyme that specifically digests the glycosidic linkages may be a hydrolase.

Said biodegradable linker may be or may comprise dextran and said enzyme that specifically digests dextran may be dextranase.

In a preferred embodiment of the invention, said modulatory agents comprise an antibody or antigen binding fragment thereof specific for CD3 and/or an antibody or antigen binding fragment thereof specific for CD28 that are directly coupled via a biodegradable linker, wherein said biodegradable linker is degraded by adding an enzyme that specifically digests the biodegradable linker. Said biodegradable linker may be or may comprise a polysaccharide and said enzyme that specifically digests the glycosidic linkages is a Hydrolase.

Said biodegradable linker may be or may comprise dextran and said enzyme that specifically digests dextran may be dextranase.

Said modulatory agents may be selected from the group consisting of agonistic antibodies or antigen binding fragment thereof, cytokines, recombinant costimulatory molecules and small drug inhibitors. Said modulatory agents may be anti-CD3 and/or anti-CD28 antibodies or fragments thereof coupled to beads or nanostructures. The modulatory agents may be a nanomatrix, the nanomatrix comprising a) a matrix of mobile polymer chains, and b) attached to said matrix of mobile polymer chains anti-CD3 and/or anti-CD28 antibodies or fragments thereof, wherein the nanomatrix is 1 to 500 nm in size. The anti-CD3 and anti-CD28 antibodies or fragments thereof may be attached to the same or to separate matrices of mobile polymer chains. If the anti-CD3 and anti-CD28 antibodies or fragments thereof are attached to separate matrices of mobile polymer chains, fine-tuning of nanomatrices for the stimulation of the T cells is possible. The nanomatrix may be biodegradable. The nanomatrix may be of collagen, purified proteins, purified peptides, polysaccharides, glycosaminoglycans, or extracellular matrix compositions. A polysaccharide may include for example, cellulose ethers, starch, gum arabic, agarose, dextran, chitosan, hyaluronic acid, pectins, xanthan, guar gum or alginate.

Said method, wherein said method comprises the steps
a) providing said sample comprising T cells and said malignant cells
b) activation of the T cells using modulatory agents
c) Incubation of the cells of said sample with said lentiviral vector particles,
wherein said method is performed in equal or less than 144 hours, less than 120 hours, less than 96 hours, less than 72 hours, less than 48 hours, or less than 24 hours.
Said method, wherein said method comprises the steps
a) providing said sample comprising T cells and said malignant cells
b) activation of the T cells using modulatory agents
c) Incubation of the cells of said sample with said lentiviral vector particles,
d) removal of said modulatory agents,
wherein said method is performed in equal or less than 144 hours, less than 120 hours, less than 96 hours, less than 72 hours, less than 48 hours, or less than 24 hours.
Said method, wherein said provided sample comprising T cells and said malignant cells comprises at least 1 malignant cell, at least 10 malignant cells, at least 100 malignant cells, at least 1,000 malignant cells, at least 10,000 malignant cells, at least 100,000 malignant cells, at least 1,000,000 malignant cells or at least 10,000,000 malignant cells.

Said method, wherein the ratio of said malignant cells in said provided sample comprising T cells and said malignant cells is less than 50%, less than 40%, less than 30%, 20%, less than 10%, less than 5%, less than 1%, less than 0.1%, less than 0.01%, less than 0.001% or less than 0.0001%.

Said method, wherein the ratio of said malignant cells to all cells in said provided sample comprising T cells and said malignant cells is below the detection level of the method quantifying said malignant cells.

Said method, wherein said method to quantify said malignant cells is flow cytometry.

Said method, wherein said sample comprising T cells and said malignant cells may be enriched before said incubation for CD4 positive and/or CD8 positive T cells by using CD4 and/or CD8 as positive selection marker, thereby reducing the number of malignant cells in said sample.

The additional step of said enrichment of CD4 and/or CD8 positive T cells within said method may further reduce the number of available malignant cells in said provided sample at least for the factor 10, 100, 1000 or 10000.

Said enrichment of CD4+ and/or CD8+ T cells from the provided sample may be performed by a separation step. Said separation may be performed by flow cytometry methods (fluorescence activated cell sorting) such as FACSorting, magnetic cell separation such as MACS or by microchip based cell sorting such as MACSQuant® Tyto®.

Preferred is the use of a magnetic cell separation step.

Alternatively, CD3 or CD62L may be used for enrichment of T cells.

Said method, wherein said enrichment of CD4 and/or CD8 positive T cells may be performed by magnetic cell separation steps comprising:
i) contacting the T cells with magnetic particles that are directly or indirectly coupled to antibodies or antigen binding fragments thereof specific for CD4 and/or CD8, wherein said magnetic particles and said antibodies or antigen binding fragments thereof coupled thereto can be removed
ii) separating the CD4 and/or CD8 positive T cells in a magnetic field
iii) removal of said magnetic particles from the enriched T cells after the separation.
Said method, wherein said enrichment of CD4 and/or CD8 positive T cells may be performed by magnetic cell separation steps comprising:
i) contacting the T cells with magnetic particles that are directly or indirectly coupled to antibodies or antigen binding fragments thereof specific for CD4 and/or CD8, wherein said magnetic particles and said antibodies or antigen binding fragments thereof coupled thereto can be removed by washing
ii) separating the CD4 and/or CD8 positive T cells in a magnetic field
iii) removal of said magnetic particles from the enriched T cells after the separation step by washing.
Said method, wherein said enrichment of CD4 and/or CD8 positive T cells may be performed by magnetic cell separation steps comprising:
i) contacting the T cells with magnetic particles that are directly or indirectly coupled to antibodies or antigen binding fragments thereof specific for CD4 and/or CD8, wherein said magnetic particles and said antibodies or antigen binding fragments thereof coupled thereto can be disrupted chemically and/or enzymatically ii) separating the CD4 and/or CD8 positive T cells in a magnetic field iii) removal of said magnetic particles from the enriched T cells after the separation step by chemical and/or enzymatical disruption of said magnetic particles and said antibodies or antigen binding fragments thereof coupled thereto.

Said removal of said magnetic particles from the enriched T cells after the separation step by chemical and/or enzymatical disruption may be performed within the magnetic field or after removal of the magnetic field.

Methods and systems for removal of magnetic particles from a cell that have been directly or indirectly bound to said cell are well-known in the art.

Exemplary, some methods and systems for reversible labelling of a cell with magnetic particles that lead to a disruption of magnetic particles from the cells are listed here.

One strategy exploits the specific competition of a non-covalent binding interaction. US20080255004 discloses a method for reversible binding to a solid support, e.g., magnetic particle, using antibodies recognizing the target moiety which are conjugated to modified biotin like des-thiobiotin, and modified streptavidin or avidin bound to the solid support. The binding interaction of the modified binding partners is weaker compared to the strong and specific binding between biotin and streptavidin therefore facilitating the dissociation in the presence of these competitors. EP2725359B1 describes a system for reversible magnetic cell separation based on the non-covalent interaction of a ligand-PEO-Biotin-conjugate recognizing the target moiety and an anti-Biotin-antibody compromising a magnetic particle that can be released by adding the competing molecule biotin, streptavidin or an auxiliary reagent.

Said method, wherein said enrichment of CD4 and/or CD8 positive T cells may be performed by magnetic cell separation step comprising:

i) contacting the T cells with magnetic particles that may be indirectly coupled via a linker to antibodies or antigen binding fragments thereof specific for CD4 and/or CD8, wherein said magnetic particles and said antibodies or antigen binding fragments thereof coupled thereto may be removed by adding a competing agent that competes with the binding of said linker to said antibodies or antigen binding fragments thereof ii) separating the CD4 and/or CD8 positive T cells in a magnetic field iii) removal of said magnetic particles from the enriched T cells after the separation step by adding the competing agent.

Said method, wherein said competing agent may be biotin, streptavidin or an auxiliary reagent.

Beside these competitive release mechanisms, the removal of labelling is mentioned by mechanical agitation, chemically cleavable or enzymatically degradable linkers. WO 96/31776 describes a method to release after separation magnetic particles from target cells by enzymatically cleaving a moiety of the particle coating, or a moiety present in the linkage group between the coating and the antigen recognizing moiety. An example is the application of magnetic particles coated with dextran and/or linked via dextran to the antigen recognizing moiety. Subsequent cleavage of the isolated target cells from the magnetic particle is initiated by the addition of the dextran-degrading enzyme dextranase. A related method in EP3037821A1 discloses the detection and separation of a target moiety according to, e.g. a fluorescence signal, with conjugates having an enzymatically-degradable spacer.

Recently, the interest grew in techniques utilizing antigen recognizing moieties whose binding to the target moiety is characterized by a low-affinity constant. To ensure a specific and stable labelling with those low-affinity antigen recognizing moieties the structure of the labelling conjugate has to comprise a multimerization of the antigen recognizing moiety providing high avidity. Upon disruption of the multimerization the low-affinity antigen recognizing moiety can dissociate from the target moiety therefore providing the opportunity to release at its best the detection moiety and the antigen recognizing moiety from the target moiety.

This reversible multimer staining was first described in U.S. Pat. No. 7,776,562 respectively U.S. Pat. No. 8,298,782 wherein the multimerization is build up by a non-covalent binding interaction. Exemplary, low affinity peptide/MHC-monomers having a StreptagII are multimerized with strep-tactin and the multimerization is reversible upon addition of the competing molecule biotin.

The method was revised in U.S. Pat. No. 9,023,604 regarding the characteristics of the antigen recognizing moiety respectively receptor binding reagent to enable reversible labelling. Receptor binding reagents characterized by a dissociation rate constant about $0.5 \times 10^{-4}$ sec-1 or greater with a binding partner Care multimerized by a multimerization reagent with at least two binding sites Z interacting reversibly, non-covalently with the binding partner C to provide complexes with high avidity for the target antigen. The detectable label is bound to the multivalent binding complex. Reversibility of multimerization is initiated upon disruption of the binding between binding partner C and the binding site Z of the multimerization reagent. For example, in multimers of Fab-StreptagII/Streptactin, multimerization can be reversed by the competitor Biotin.

In EP0819250B 1 a method is provided for releasing magnetic particles bound to a cell surface through an affinity reagent, e.g. an antibody or antigen binding fragment thereof. The magnetic particle is released through action of a glycosidase specific for a glycosidic linkage present in at least one of (a) the coating of the particle and (b) a linkage group between the coating and the affinity reagent.

In EP3336546A1 a method is disclosed for detecting a target moiety in a sample of biological specimens by:

a) providing at least one conjugate with the general formula (I)

$$A_n\text{-}P\text{-}B_m\text{-}C_q\text{-}X_o \tag{I}$$

with A: antigen recognizing moiety;
P: enzymatically degradable spacer;
B: first binding moiety
C second binding moiety
X: detection moiety;
n, m, q, o integers between 1 and 100,
wherein B and C are non-covalently bound to each other and A and B are covalently bound to P b) labelling the target moiety recognized by the antigen recognizing moiety A with at least one conjugate c) detecting the labelled target moiety via detecting moiety X d) cleaving $C_q\text{-}X_o$ by disrupting the non-covalent bond between $B_m$ and $C_q$ from the labelled target moiety e) cleaving the binding moiety $B_m$ from the labelled target moiety by enzymatically degrading spacer P.

The method of EP3336546A1 may be utilized not only for detecting target moieties i.e. target cells expressing such target moieties, but also for isolating the target cells from a sample of biological specimens. The isolating procedures make use of detecting the target moieties. For example, the detection of a target moiety by fluorescence may be used to trigger an appropriate separation process as performed on FACS or TYTO separation systems. The method disclosed in EP3336546A1 may also be used for a magnetic cell separation process, wherein magnetic particles may be used in a magnetic field instead of the detection moieties described therein.

In a preferred embodiment of the invention, said magnetic particles that are directly coupled to antibodies or antigen binding fragments thereof specific for CD4 and/or CD8 are coupled via a biodegradable linker, wherein said biodegradable linker is degraded by adding an enzyme that (specifically) digests the biodegradable linker. Said biodegradable linker may be or may comprise a polysaccharide and said enzyme that (specifically) digests the glycosidic linkages is a hydrolase. Said biodegradable linker may be or may comprise dextran and said enzyme that (specifically) digests dextran may be dextranase.

In another preferred embodiment of the invention, said magnetic particles that are indirectly coupled to antibodies or antigen binding fragments thereof, such as Fabs, specific for CD4 and/or CD8 are coupled via two components i) a linker, such as dextran, that is coupled to a tag such as PEO-Biotin or said Fabs specific for CD4 and/or CD8 that are coupled to a tag such as PEO-biotin, ii) a magnetic particle that is coupled to an antibody or antigen binding fragment thereof specific for said tag, e.g. biotin, wherein after combining component i and ii and after contacting the T cells with said indirectly coupled magnetic particle, the magnetic particle may be disrupted (removed) by adding a competing agent that competes with said tag, e.g. biotin (as a competitor).

In another preferred embodiment of the invention, said magnetic particles that are indirectly coupled to antibodies or antigen binding fragments thereof, such as Fabs, specific for CD4 and/or CD8 are coupled via two components i) a biodegradable linker, such as dextran, that is coupled to a tag such as PEO-Biotin, ii) a magnetic particle that is coupled to an antibody or antigen binding fragment thereof specific for said tag, e.g. biotin, wherein after combining component i and ii and after contacting the T cells with said indirectly coupled magnetic particle, the magnetic particle may be disrupted from said T cell by adding an enzyme that specifically digests the biodegradable linker such as dextranase and/or by adding a competing agent that competes with said tag, e.g. biotin (as a competitor).

Said method, wherein said competing agent is biotin, streptavidin or an auxiliary reagent.

Said method, wherein said sample comprising T cells and said malignant cells is depleted of malignant cells by using said antigen that is expressed on the surface of said malignant cells as a negative selection marker.

Said method, wherein said sample comprising T cells and said malignant cells is additionally to said enrichment step of CD4+ and/or CD8+ T cells depleted of said malignant cells by using said antigen that is expressed on the surface of said malignant cells as a negative selection marker.

The addition step of depleting malignant cells within said method may further reduce the number of available malignant cells in said provided sample at least for the factor 10, 100, 1000 or 10000.

In another aspect the present invention provides a combination of compositions comprising a first composition and a second composition, wherein said first composition comprises i) transduced T cells of a subject, wherein said transduced T cells express a CAR comprising an antigen binding domain, wherein the antigen binding domain of said CAR specifically binds to a tag of a tagged polypeptide ii) non-transduced malignant cells of the blood system of said subject that are not derived from T cells, and wherein said second composition comprises said tagged polypeptide, wherein said tagged polypeptide specifically binds to an antigen expressed on the surface of said malignant cells.

Importantly, the malignant cells are not added by an operator to the first composition, they are naturally present in the blood systems of said subject that provides the T cells to be transduced to express said CAR.

Said non-transduced malignant cells of the blood system of said subject that are not derived from T cells, wherein said malignant cells have not been separated by positive or negative selection methods using Magnetic-activated cell sorting (MACS).

Said non-transduced malignant cells of the blood system of said subject that are not derived from T cells, wherein said cells are untouched cells., i.e. they have not been separated by positive selection methods using antibodies or antigen binding fragments thereof specific for said antigen or another tumor associated antigen expressed on the surface of said malignant cells.

This combination of compositions has the benefit of comprising in said first composition transduced T cells expressing a CAR and simultaneously said malignant cells that are also present in said subject and should be eliminated by these transduced T cells in an in-vivo immunotherapy, i.e. both the transduced CAR T cells and the malignant cells are from the same subject. In said first composition the transduced T cells are not able to induce anti-tumoral activity towards the malignant cells due to missing specificity of the antigen binding domain of the CAR for the antigen expressed on the surface of said malignant cells. But the addition of the second composition induces antigen recognition and subsequent cytolytic activity: the tagged polypeptide binds to the antigen binding domain of the CAR and allows indirect binding of the CAR to the antigen expressed on the malignant cells, thereby triggering the immune response of the CAR T cell and leading to the death of the malignant cells.

Adding the second composition or a portion thereof to the first composition or a portion thereof allows to more reliably predict the outcome of the immunotherapy in said subject. It is possible to analyze in-vitro the efficacy of eliminating the malignant cells by the transduced T cells. Further CAR T cell functionality might also be evaluated based on the levels of calcium release, cytokine production, differentiation and activation. On the other hand, it may also be analyzed how the malignant cells (the primary malignant cells, not normally used immortalized cell lines) react to the presence of the CAR T cells, e.g. possible down-regulation of the antigen, or de-novo expression of resistance a marker. Adding a portion of the second composition to a portion of the first composition may also be useful for determining and adjusting the required CAR T cell dose to achieve therapeutic efficacy without induction of dose-related toxicity for in-vivo application in said subject.

The behavior and/or the effects of the transduced T cells and/or the malignant cells in a sample wherein the second composition or a portion thereof has been added to the first composition or a portion thereof may be analyzed and/or observed by using flow cytometry, microscopy, live cell imaging, in vivo imaging, high content imaging, sequencing, qPCR, fluorescence microscopy, cytokine expression levels.

Said combination of compositions for use in treatment of a malignancy in said subject in need thereof, wherein said malignancy is caused by said malignant cells in the blood system of said subject.

Said combination of compositions for use in a method of treating a malignancy in said subject in need thereof, wherein said malignancy is caused by said malignant cells in the blood system of said subject, the method comprising
    i) administering to said subject said first composition, and
    ii) administering to said subject said second composition.

Said combination of compositions, wherein said transduced T cells and said non-transduced malignant cells of said first composition are obtained by the method comprising the steps
    a) providing a sample comprising T cells and said malignant cells of a blood system of a subject that are not derived from T cells
    b) Incubation of the cells of said sample with lentiviral vector particles, wherein
said lentiviral vector particles are pseudotyped with an envelope protein selected from the group consisting of BaEV env, VSV-G, RD114-TR, GALV-TR, MV-H/F, NiV-G/F, and Ampho-MLV env, and wherein said lentiviral vector particles comprise a nucleic acid encoding a chimeric antigen receptor (CAR) comprising an antigen binding domain, wherein said antigen binding domain of said CAR specifically binds to a tag of a tagged polypeptide, wherein said polypeptide binds specifically to an antigen expressed on the surface of said malignant cells.

Said combination of compositions, wherein said transduced T cells and said non-transduced malignant cells of said first composition are obtained by the methods as disclosed herein.

Said combination of compositions, wherein said first composition comprises transduced malignant cells of the blood system of said subject that are not derived from T cells and non-transduced malignant cells of the blood system of said subject that are not derived from T cells in a ratio of less than 1 to 100,000, less than 1,000,000, less than 1 to 10,000,000, less than 1 to 100,000,000 or less than 1 to 1,000,000,000.

Said combination of compositions, wherein said first composition comprises less than 10%, less than 1%, less than 0.01%, less than 0.001%, less than 0.0001%, less than 0.00001%, less than 0.000001%, less than 0.0000001% non-transduced malignant cells of all cells of said first composition.

Said combination of compositions, wherein said ratio of transduced T cells to non-transduced malignant cells is higher than 1 to 10, higher than 1 to 1, higher than 10 to 1, higher than 100 to 1, higher than 1,000 to 1, higher than 10,000 to 1, higher than 100,000 to 1, higher than 1,000,000 to 1, higher than 10,000,000 to 1.

Said combination of compositions, wherein said ratio of transduced T cells to transduced malignant cells is higher than 100 to 1, higher than 1,000 to 1, higher than 10,000 to 1, higher than 100,000 to 1, higher than 1,000,000 to 1, higher than 10,000,000 to 1, higher than 100,000,000 to 1, higher than 1,000,000,000 to 1, higher than 10,000,000,000 to 1.

Said combination of compositions, wherein said first composition comprises at least 1 non-transduced malignant cell, at least 10 non-transduced malignant cells, at least 100 non-transduced malignant cells, at least 1,000 non-transduced malignant cells, at least 10,000 non-transduced malignant cells, at least 100,000 non-transduced malignant cells, at least 1,000,000 non-transduced malignant cells, at least 100,000,000 non-transduced malignant cells, at least 1,000,000,000 non-transduced malignant cells, at least 10,000,000,000 non-transduced malignant cells.

Said combination of compositions for use in an in-vitro method for assessing the outcome of the treatment of said malignancy in said subject.

Said combination of compositions, wherein said combination of compositions comprises a third composition comprising a detection agent, wherein said detection agent is an antibody or antigen binding fragment thereof specific for said antigen expressed on said malignant cells, an antibody or antigen binding fragment thereof specific for another tumor associated antigen expressed on said malignant cells, or an antibody or antigen binding fragment thereof specific for a cytokine secreted by said transduced T cells induced by the immune response triggered by the contact between said transduced T cell and said malignant cells, wherein said detection agent is coupled to a fluorophore or magnetic particle.

Said antibody or antigen binding fragment thereof may be selected from the group consisting of an antibody or antigen binding fragment thereof specific for IL-2, IFN-gamma and TNF-alpha.

Said combination of compositions comprising said three components for use in a method of analyzing the antitumoral response of said transduced T cells.

In one aspect the present invention provides the use of a combination of compositions comprising a first composition and a second composition for assessing the outcome of the treatment of a malignancy caused by malignant cells in a subject by CAR T cell therapy, wherein said first composition comprises
    i) transduced T cells of a subject, wherein said transduced T cells express a CAR comprising an antigen binding domain, wherein the antigen binding domain of said CAR specifically binds to a tag of a tagged polypeptide
    ii) non-transduced malignant cells of the blood system of said subject that are not derived from T cells,
    and wherein said second composition comprises said tagged polypeptide, wherein said tagged polypeptide specifically binds to an antigen expressed on the surface of said malignant cells.

Said use of a combination of compositions wherein said combination comprises the third composition as disclosed herein.

An in-vitro method for assessing the outcome of the treatment of a malignancy in a subject by CAR T cell immunotherapy in said subject in need thereof by use of a combination of compositions (as disclosed herein) wherein said first composition comprises
    i) transduced T cells, wherein said transduced T cells express a CAR comprising an antigen binding domain, wherein the antigen binding domain of said CAR binds specifically to a tag of a tagged polypeptide
    ii) non-transduced malignant cells of the blood system of said subject that are not derived from T cells,
    and wherein said second composition comprises said tagged polypeptide, wherein said tagged polypeptide binds specifically to an antigen expressed on the surface of said malignant cells, the method comprising i) adding said second composition or a portion thereof to said first composition or a portion thereof, thereby generating a sample comprising transduced T cells, wherein said CAR binds to said antigen expressed on the surface of said malignant cells, ii) analyzing the antitumoral activities of said transduced T cells in said sample towards said malignant cells, wherein when the lysis of said malignant cells by said transduced T cells in said sample is increased as compared to the lysis in said first composition alone is indicative of a good outcome.

Said in-vitro method, wherein said lysis is increased at least 2-fold, at least 5-fold, at least 10-fold, at least 20-fold, at least 50-fold.

An in-vitro method for assessing the outcome of the treatment of a malignancy in a subject by CAR T cell immunotherapy in said subject in need thereof by use of a combination of compositions (as disclosed herein) wherein said first composition comprises i) transduced T cells, wherein said transduced T cells express a CAR comprising an antigen binding domain, wherein the antigen binding domain of said CAR binds specifically to a tag of a tagged polypeptide ii) non-transduced malignant cells of the blood system of said subject that are not derived from T cells, and wherein said second composition comprises said tagged polypeptide, wherein said tagged polypeptide binds specifically to an antigen expressed on the surface of said malignant cells, the method comprising i) adding said second composition or a portion thereof to said first composition or a portion thereof, thereby generating a sample comprising transduced T cells, wherein said CAR binds to said antigen expressed on the surface of said malignant cells, ii) analyzing the antitumoral activities of said transduced T cells in said sample towards said malignant cells, wherein when the release of the cytokine IL-2, INF-gamma or TNF-alpha is increased as compared to the release of said cytokine in said first composition alone is indicative of a good outcome. Said in-vitro method, wherein said release of said cytokine is increased at least 2-fold, at least 5-fold, at least 10-fold, at least 20-fold, at least 50-fold, at least 100-fold, at least 1000-fold.

In a further aspect the present invention provides a method of reducing the efficiency of transducing malignant cells of the blood system of a subject that are not derived from T cells with lentiviral vector particles without reducing the efficiency of transducing T cells in a sample comprising T cell and said malignant cells, wherein said lentiviral vector particles are pseudotyped with an envelope protein selected from the group consisting of BaEV env, VSV-G, RD114-TR, GALV-TR, MV-H/F, NiV-G/F, and Ampho-MLV env, and wherein said lentiviral vector particles comprise a nucleic acid encoding a CAR and a gene expression system, wherein said CAR is expressed under the control of said gene expression system allowing the expression of said CAR in the transduced cells, wherein said CAR is not displayed on the lentiviral vector particles, wherein said CAR has an antigen binding domain that binds specifically to an antigen that is expressed on the surface of said malignant cells, the method comprising a) providing said sample comprising T cells and said malignant cells b) Incubation of the cells of said sample with said lentiviral vector particles, thereby generating a sample comprising said transduced T cells, wherein the efficiency of transducing said malignant cells induced by said incubation is reduced compared to the efficiency of transducing said malignant cells of said sample comprising T cells and said malignant cells wherein/when said lentiviral vector particles are replaced by lentiviral vector particles that do not comprise said gene expression system thereby generating lentiviral vector particles displaying said CAR on the surface of said lentiviral vector particles that has an antigen binding domain specific for an antigen that is expressed on the surface of said malignant cells.

Said method, wherein said gene expression system is i) an inducible gene expression system and wherein when an induction agent is administered to a cell being transduced with said inducible gene expression system, the gene expression system is induced and said CAR is expressed on the surface of said transduced cell, or ii) a tissue-specific promoter operatively linked to said CAR, wherein said tissue-specific promotor is transcriptional active in T cells.

In certain embodiments, the inducible gene expression system comprises: (a) a first nucleic acid comprising a constitutive promoter operably linked to a nucleic acid sequence encoding a transactivator protein; and (b) a second nucleic acid comprising an inducible promoter operably linked to a nucleic acid sequence encoding the exogenous receptor, i.e. the CAR, wherein the second nucleic acid is in reverse orientation to the first nucleic acid.

In certain embodiments, the transactivator protein is a reverse Tet repressor (rTetR). In certain embodiments, the transactivator protein is a reverse tetracycline-controlled transactivator protein (rtTA). In certain embodiments, the transactivator protein is a Tet-On 3G transactivator protein. In other embodiments, the inducible promoter comprises a Tet operator sequence. In other embodiments, the inducible promoter comprises one or more repeats of the Tet operator sequence. In other embodiments, the inducible promoter is a TRE3GS promoter.

In other embodiments, the constitutive promoter drives constitutive expression of the transactivator protein. In one embodiment, the constitutive promoter is a human constitutive promoter, e.g., a human phosphogly cerate kinase 1 (PGK1) promoter or a human elongation factor 1 alpha (EF1a) promoter.

In other embodiments, the induction agent is tetracycline or a derivative thereof, e.g., doxycycline. In certain embodiments, the inducible gene expression system encodes a reverse Tet transactivator (rtTA) fusion protein and comprises at least one promoter fused downstream of at least one Tet-operator sequence.

In certain aspects the genetically modified immune cells comprise a tetracycline (Tet)-On inducible gene expression system, wherein the Tet-On inducible gene expression system comprises a reverse Tet transactivator (rtTA) fusion protein and at least one promoter fused downstream of at least one Tet-operator sequence.

In certain embodiments, the disclosure provides an isolated nucleic acid encoding an exogenous receptor i.e. the CAR, the expression of which is under the control of a tetracycline (Tet)-On inducible gene expression system, wherein the Tet-On inducible gene expression system comprises a reverse Tet transactivator (rtTA) fusion protein and at least one promoter fused downstream of at least one Tet-operator sequence.

In other embodiments, the disclosure provides a genetically modified T cell comprising an exogenous nucleic acid encoding an exogenous receptor i.e. the CAR, under the control of a tetracycline (Tet)-On inducible gene expression system, wherein the Tet-On inducible gene expression system comprises a reverse Tet transactivator (rtTA) fusion protein and at least one promoter fused downstream of at least one Tet-operator sequence, wherein when doxycycline (Dox) is administered to the cell, the gene expression system is induced and the CAR is expressed. In other embodiments, the inducible promoter induces expression of the exogenous CAR is in a dose-dependent manner with respect to the amount of the induction agent present. In certain embodiments, withdrawal of the induction agent results in a reduction in the expression of the exogeneous receptor.

In certain embodiments, the transactivator protein is a chimeric transcription factor. In certain embodiments, the transactivator protein comprises an inducible domain, a DNA binding domain and transactivation domain. In certain embodiments, the inducible domain is the estrogen receptor. In certain embodiments, the induction agent is tamoxifen. In certain embodiments, the induction agent is 4-hydroxytamoxifen.

In other embodiments, the transactivator protein is a two-component transcription factor that is dimerized with a small molecule.

In other embodiments, the small molecule is rapamycin and the dimerizing domain is FKBP.

In certain embodiments, the CAR is degraded by the activity of proteases, wherein the activity of said proteases is inhibited by the addition of a specific protease inhibitor.

In other embodiments, the CAR is expressed as a fusion protein operably linked to protease, wherein said CAR and said protease are fused with a linker motif and said protease is specific for said linker motif.

In other embodiments, the activity of said protease induces the activity of said CAR.

In other embodiments, the activity of said protease is inhibited by the addition of an inhibitor specific for said protease.

In another aspect the present invention provides a combination of compositions comprising a first composition and a second composition, wherein said first composition comprises i) transduced T cells of a subject, wherein said transduced T cells comprise a nucleic acid encoding a CAR and an inducible gene expression system, wherein when an induction agent is administered to a cell being transduced with said inducible gene expression system, the gene expression system is induced and said CAR is expressed on the surface of said transduced cell, wherein said CAR has an antigen binding domain that binds specifically to an antigen that is expressed on the surface of malignant cells of said subject, ii) non-transduced malignant cells of the blood system of said subject that are not derived from T cells, and wherein said second composition comprises said induction agent.

Said combination of compositions, wherein said inducible gene expression system may comprise the estrogen receptor as an inducible domain and wherein tamoxifen may be said induction agent.

Said combination of compositions for use in treatment of a malignancy in said subject in need thereof, wherein said malignancy may be caused by said malignant cells in the blood system of said subject.

Said combination of compositions for use in a method of treating a malignancy in said subject in need thereof, wherein said malignancy may be caused by said malignant cells in the blood system of said subject, the method comprising i) administering to said subject said first composition, and ii) administering to said subject said second composition.

Said combination of compositions, wherein said transduced T cells and said non-transduced malignant cells of said first composition may be obtained by the method comprising the steps a) providing a sample comprising T cells and said malignant cells of a blood system of a subject that are not derived from T cells b) Incubation of the cells of said sample with lentiviral vector particles, wherein said lentiviral vector particles are pseudotyped with an envelope protein selected from the group consisting of BaEV env, VSV-G, RD114-TR, GALV-TR, MV-H/F, NiV-G/F, and Ampho-MLV env, and wherein said lentiviral vector particles comprise a nucleic acid encoding a CAR and an inducible gene expression system, wherein when an induction agent is administered to a cell being transduced with said inducible gene expression system, the gene expression system is induced and said CAR is expressed on the surface of said transduced cell, wherein said CAR has an antigen binding domain that binds specifically to an antigen that is expressed on the surface of malignant cells of said subject.

Said combination of compositions, wherein said transduced T cells and said non-transduced malignant cells of said first composition are obtained by the methods as disclosed herein.

Said combination of compositions for use in an in-vitro method for assessing the outcome of the treatment of said malignancy in said subject.

Said combination of compositions, wherein said combination of compositions comprises a third composition comprising a detection agent, wherein said detection agent is an antibody or antigen binding fragment thereof specific for said antigen expressed on said malignant cells, an antibody or antigen binding fragment thereof specific for another tumor associated antigen expressed on said malignant cells, or an antibody or antigen binding fragment thereof specific for a cytokine secreted by said transduced T cells induced by the immune response triggered by the contact between said transduced T cell and said malignant cells, wherein said detection agent is coupled to a fluorophore or magnetic particle.

Said antibody or antigen binding fragment thereof may be selected from the group consisting of an antibody or antigen binding fragment thereof specific for IL-2, IFN-gamma or TNF-alpha.

Said combination of compositions comprising said three components for use in a method of analyzing the antitumoral response of said transduced T cells.

In one aspect the present invention provides the use of a combination of compositions comprising a first composition and a second composition for assessing the outcome of the treatment of a malignancy caused by malignant cells in a subject by CAR T cell therapy, wherein said first composition comprises i) transduced T cells of said subject, wherein said transduced T cells comprise a nucleic acid encoding a CAR and an inducible gene expression system, wherein when an induction agent is administered to a cell being transduced with said inducible gene expression system, the gene expression system is induced and said CAR is expressed on the surface of said transduced cell, wherein said CAR has an antigen binding domain that binds specifically to an antigen that is expressed on the surface of malignant cells of said subject, ii) non-transduced malignant cells of the blood system of said subject that are not derived from T cells, and wherein said second composition comprises said induction agent.

Said use of a combination of compositions wherein said combination comprises the third composition as disclosed herein.

In another aspect the present invention provides an in-vitro method for assessing the outcome of the treatment of a malignancy in a subject by CAR T cell immunotherapy in said subject in need thereof by use of a combination of compositions wherein said first composition comprises i) transduced T cells of a subject, wherein said transduced T cells comprise a nucleic acid encoding a CAR and an inducible gene expression system, wherein when an induction agent is administered to a cell being transduced with said inducible gene expression system, the gene expression system is induced and said CAR is expressed on the surface of said transduced cell, wherein said CAR has an antigen binding domain that binds specifically to an antigen that is expressed on the surface of malignant cells of said subject, ii) non-transduced malignant cells of the blood system of said subject that are not derived from T cells, and wherein said second composition comprises said induction agent, the method comprising i) adding said second composition or a portion thereof to said first composition or to a portion thereof, thereby generating a sample comprising transduced T cells expressing said CAR, wherein said CAR binds to said antigen expressed on the surface of said malignant cells, ii) analyzing the antitumoral activities of said transduced T cells in said sample towards said malignant cells, wherein when the lysis of said malignant cells by said transduced T cells in said sample is increased as compared to the lysis in said first composition alone is indicative of a good outcome.

Said in-vitro method, wherein said lysis in increased at least 2-fold, at least 5-fold, at least 10-fold, at least 20-fold, at least 50-fold.

In another aspect the present invention provides an in-vitro method for assessing the outcome of the treatment of a malignancy in a subject by CAR T cell immunotherapy in said subject in need thereof by use of a combination of compositions wherein said first composition comprises i) transduced T cells of a subject, wherein said transduced T cells comprise a nucleic acid encoding a CAR and an inducible gene expression system, wherein when an induction agent is administered to a cell being trans-duced with said inducible gene expression system, the gene expression system is induced and said CAR is expressed on the surface of said transduced cell, wherein said CAR has an antigen binding domain that binds specifically to an antigen that is expressed on the surface of malignant cells of said subject, ii) non-transduced malignant cells of the blood system of said subject that are not derived from T cells, and wherein said second composition comprises said induction agent, the method comprising i) adding said second composition or a portion thereof to said first composition or to a portion thereof, thereby generating a sample comprising transduced T cells expressing said CAR, wherein said CAR binds to said antigen expressed on the surface of said malignant cells, ii) analyzing the antitumoral activities of said transduced T cells in said sample towards said malignant cells, wherein when the release of the cytokine IL-2, Interferon-gamma or TNF-alpha is increased as compared to the release of said cytokine in said first composition alone is indicative of a good outcome.

Said in-vitro method, wherein said release of said cyto-kines is increased at least 2-fold, at least 5-fold, at least 10-fold, at least 20-fold, at least 50-fold, at least 100-fold, at least 1000-fold.

In a further aspect the present invention provides a method of reducing the efficiency of transducing malignant cells of the blood system of a subject that are not derived from T cells with lentiviral vector particles without reducing the efficiency of transducing T cells in a sample comprising T cell and said malignant cells, wherein said lentiviral vector particles are pseudotyped with an envelope protein selected from the group consisting of BaEV env, VSV-G, RD114-TR, GALV-TR, MV-H/F, NiV-G/F, and Ampho-MLV env, and wherein said lentiviral vector particles comprise a nucleic acid encoding a CAR, wherein said CAR is not displayed on the lentiviral vector particles, wherein said CAR has an antigen binding domain that binds specifically to an antigen that is expressed on the surface of said malignant cells, the method comprising a) providing said sample comprising T cells and said malignant cells b) Incubation of the cells of said sample with said lentiviral vector particles, thereby generating a sample comprising said transduced T cells, wherein the efficiency of transducing said malignant cells induced by said incubation is reduced compared to the efficiency of transducing said malignant cells of said sample comprising T cells and said malignant cells wherein/when said lentiviral vector particles are replaced by lentiviral vector particles that display said CAR on the surface of said lentiviral vector particles that has an antigen binding domain specific for an antigen that is expressed on the surface of said malig-nant cells, wherein said lentiviral vector particles that do not display said CAR on the lentiviral vector par-ticles have been generated in a packaging cell line that do not express said CAR.

Said packaging cell line may be negative for the tran-scription factor(s) that may be responsible for inducing the CAR expression in said packaging cell line, wherein the absence of said transcription factor(s) does/do not inhibit transcription of the lentiviral vector genome or wherein said packaging cell line may express (a) transcriptional repressor (s) inhibiting CAR expression in said packaging cell line, wherein the presence of said transcriptional repressor(s) does/do not inhibit transcription of the lentiviral vector genome.

In one embodiment it may be sufficient to knock-down/out one transcription factor to prevent the CAR expression in the packaging cell line, in another embodiment two or more transcription factors of the packaging cell line may be knocked-down/out to prevent said CAR expression.

Said transcription factor may be e.g. NF-κB, TEF, AP-1 or may be selected from the group consisting of HSF, STAT, GATA, and C/EBP family.

In one embodiment it may be sufficient to express one transcriptional repressor to prevent the CAR expression in the packaging cell line, in another embodiment two or more transcriptional repressors may be expressed by the packaging cell line to prevent said CAR expression.

Said transcriptional repressor may be e.g. KRAB domain of Kox, CS domain of HP1α or the WRPW domain of Hes1.

Said packaging cell line may be selected from the group consisting of

HEK 293, HEK 293T, HEK EBNA, HEK 293F, HEK 293FT and HEK 293-S.

In one aspect the present invention provides a method for the generation of a sample comprising transduced T cells encoding a chimeric antigen receptor (CAR) with lentiviral vector particles from a sample comprising T cells and malignant cells, wherein said lentiviral vector particles may be pseudotyped with an envelope protein selected from the group consisting of BaEV env, VSV-G, RD114-TR, GALV-TR, MV-H/F, NiV-G/F, and Ampho-MLV env, and wherein said lentiviral vector particles may comprise a nucleic acid encoding a chimeric antigen receptor (CAR) comprising an antigen binding domain, wherein said antigen binding domain of said CAR may bind specifically to a tag of a tagged polypeptide, wherein said polypeptide may bind to an antigen expressed on the surface of said malignant cells, the method comprising a) Providing a sample comprising T cells and said malignant cells
   b) Incubation of the cells of said sample with said lentiviral vector particles, thereby generating said sample comprising said transduced T cells.

Said method, wherein the efficiency of transducing said malignant cells induced by said incubation is reduced compared to the efficiency of transducing said malignant cells of said sample comprising T cells and said malignant cells wherein said lentiviral vector particles are replaced by lentiviral vector particles comprising a nucleic acid encoding a CAR, wherein said CAR has an antigen binding domain specific for an antigen that is expressed on the surface of said malignant cells, thereby generating lentiviral vector particles comprising said CAR that has an antigen binding domain specific for an antigen that is expressed on the surface of said malignant cells.

Said method, wherein the efficiency of transducing said T cells is not reduced compared to said replacement of the lentiviral vector particles.

Said method, wherein the efficiency of transducing said T cells is increased for at least 10%, for at least 20%, for at least 30%, for at least 40%, for at least 50%, for at least 60%, for at least 70%, for at least 80% compared to said replacement of the lentiviral vector particles.

In one aspect the present invention provides a method for the generation of a sample comprising transduced T cells encoding a chimeric antigen receptor (CAR) with lentiviral vector particles from a sample comprising T cells and malignant cells, wherein said lentiviral vector particles may be pseudotyped with an envelope protein selected from the group consisting of BaEV env, VSV-G, RD114-TR, GALV-TR, MV-H/F, NiV-G/F, and Ampho-MLV env, and wherein said lentiviral vector particles comprise a nucleic acid encoding a CAR and a gene expression system, wherein said CAR is expressed under the control of said gene expression system allowing the expression of said CAR in the transduced cells, wherein said CAR is not displayed on the lentiviral vector particles, wherein said CAR has an antigen binding domain that binds specifically to an antigen that is expressed on the surface of said malignant cells, the method comprising a) providing said sample comprising T cells and said malignant cells
   b) Incubation of the cells of said sample with said lentiviral vector particles, thereby generating a sample comprising said transduced T cells.

Said method, wherein the efficiency of transducing said malignant cells induced by said incubation is reduced compared to the efficiency of transducing said malignant cells of said sample comprising T cells and said malignant cells wherein/when said lentiviral vector particles are replaced by lentiviral vector particles that do not comprise said gene expression system thereby generating lentiviral vector particles displaying said CAR on the surface of said lentiviral vector particles that has an antigen binding domain specific for an antigen that is expressed on the surface of said malignant cells.

Said method, wherein the efficiency of transducing said T cells is not reduced compared to said replacement of the lentiviral vector particles.

Said method, wherein the efficiency of transducing said T cells is increased for at least 10%, for at least 20%, for at least 30%, for at least 40%, for at least 50%, for at least 60%, for at least 70%, for at least 80% compared to said replacement of the lentiviral vector particles.

The methods as disclosed herein, wherein said methods may be automated methods, preferentially performed in a closed system.

The methods as disclosed herein can be fully implemented as an automated process, preferentially in a closed system under GMP conditions.

Such a closed system allows to operate under GMP or GMP-like conditions ("sterile") resulting in cell compositions which are clinically applicable. Such a closed system may be the CliniMACS Prodigy® (Miltenyi Biotec GmbH, Germany) This system is disclosed in WO2009/072003. But it is not intended to limit the use of the method of the present invention to the CliniMACS® Prodigy. The CliniMACS Prodigy® System is designed to automate and standardize complete cellular product manufacturing processes. It combines CliniMACS® Separation Technology (Miltenyi Biotec GmbH, Germany) with a wide range of sensor-controlled, cell processing capabilities. Prominent features of the device are:

disposable CentriCult™ Chamber enabling standardized cell processing and cultivation
   Cell enrichment and depletion capabilities, alone or combined with CliniMACS® Reagents (Miltenyi Biotec GmbH)
   Cell cultivation and cell expansion capabilities thanks to temperature and controlled $CO_2$ gas exchange.
   Final product formulation in pre-defined medium and volume
   the possibility to program the device using Flexible Programming Suite (FPS) and GAMP5 compatible programming language for customization of cell processing
   Tailor-made tubing sets for a variety of applications In one embodiment of the invention said combination of compositions are pharmaceutical cell compositions, wherein said first composition comprises i) transduced T cells of a subject, wherein said transduced T cells comprise a nucleic acid encoding a CAR and an inducible gene expression system, wherein when an induction agent is administered to a cell being trans-
duced with said inducible gene expression system, the
gene expression system is induced and said CAR is
expressed on the surface of said transduced cell,
wherein said CAR has an antigen binding domain that
binds specifically to an antigen that is expressed on the
surface of malignant cells of said subject, ii) non-transduced malignant cells of the blood system of
said subject that are not derived from T cells, and
optionally iii) a pharmaceutical carrier,
and wherein said second composition comprises said
induction agent and optionally a pharmaceutical car-
rier, or
wherein said first composition comprises i) transduced T cells of a subject, wherein said transduced
T cells express a CAR comprising an antigen binding
domain, wherein the antigen binding domain of said
CAR binds specifically to a tag of a tagged polypeptide ii) non-transduced malignant cells of the blood system of
said subject that are not derived from T cells, and
optionally iii) a pharmaceutical carrier,
and wherein said second composition comprises said
tagged polypeptide, wherein said tagged polypeptide
binds specifically to an antigen expressed on the sur-
face of said malignant cells, and optionally a pharma-
ceutical carrier.

In one embodiment, said first composition comprising T
cells expressing the "anti-tag CAR" as disclosed herein and
said second composition comprising said polypeptide spe-
cifically binding to an antigen expressed on said malignant
cells as disclosed herein may be for use in the treatment in
a subject suffering from cancer/malignancy, i.e. having said
malignant cells. The T cells of the subject may be genetically
modified in-vitro to express the CAR specific for a tag of a
tagged polypeptide as disclosed herein. These engineered
cells may be activated and expanded in-vitro to a therapeu-
tically effective population of expressing cells. In cellular
therapy these engineered cells may be infused to a recipient
in need thereof as a pharmaceutical composition (or a
formulation of a therapeutically effective population of
anti-tag CAR expressing cells), in addition to a second
pharmaceutical composition, a formulation of the tagged
polypeptide as disclosed herein. The infused cells in the
recipient may be able to kill (or at least stop growth of)
cancerous cells (malignant cells) expressing the antigen
which is recognized by the CAR system as disclosed herein.
The therapeutically effective population of anti-tag CAR
expressing T cells may be administered to the patient before
the administration of the formulation of the tagged polypep-
tide to the subject. Alternatively, the formulation of the
tagged polypeptide may be administered to the subject
before or at the same time as the administration the thera-
peutically effective population of anti-tag CAR expressing T
cells to the subject. A further variation includes in-vitro
culturing the therapeutically effective population of anti-tag
CAR expressing T cells with the tagged polypeptide of the
formulation of the tagged polypeptide prior to administra-
tion to the subject.

Populations of anti-tag-CAR-expressing T cells may be
formulated for administered to a subject using techniques
known to the skilled artisan.

Formulations comprising therapeutically effective popu-
lation(s) of anti-tag expressing CAR cells may include
pharmaceutically acceptable excipient(s) (carrier or
diluents). Excipients included in the formulations will have different purposes depending, for example, on the nature of
the tag-binding domain of the anti-tag-CAR, the (sub)
population of immune cells used, and the mode of admin-
istration. Examples of generally used excipients include,
without limitation: saline, buffered saline, dextrose, water-
for-injection, glycerol, ethanol, and combinations thereof,
stabilizing agents, solubilizing agents and surfactants, buf-
fers and preservatives, tonicity agents, bulking agents, and
lubricating agents.

A formulation of a therapeutically effective population(s)
of anti-tag expressing CAR cells may include one popula-
tion of anti-tag CAR-expressing (immune) cells, or more
than one population of anti-tag-CAR-expressing (immune)
cells. The different populations of anti-tag-CAR (immune)
cells may vary based on the identity of the tag-binding
domain, the identity of the activation domain, the identity of
the (sub)population of immune cells, or a combination
thereof.

The formulations comprising therapeutically effective
population(s) of anti-tag expressing CAR cells may be
administered to a subject using modes and techniques
known to the skilled artisan. Exemplary modes include, but
are not limited to, intravenous injection. Other modes
include, without limitation, intratumoral, intradermal, sub-
cutaneous (s.c, s.q., sub-Q, Hypo), intramuscular (i.m.),
intraperitoneal (i.p.), intra-arterial, intramedulary, intracar-
diac, intra-articular (joint), intrasynovial (joint fluid area),
intracranial, intraspinal, and intrathecal (spinal fluids).

The formulations comprising therapeutically effective
population(s) of anti-tag expressing CAR cells that are
administered to a subject comprise a number of anti-tag-
CAR-expressing cells such immune cells that is effective for
the treatment of the specific indication or disorder.

In general, formulations may be administered that com-
prise between about $1\times10^4$ and about $1\times10^{10}$ anti-tag-CAR-
expressing cells such as immune cells. In most cases, the
formulation may comprise between about $1\times10^5$ and about
$1\times10^9$ anti-tag-CAR-expressing cells such as immune cells,
from about $5\times10^5$ to about $5\times10^8$ anti-tag-CAR-expressing
cells such as immune cells, or from about $1\times10^6$ to about
$1\times10^7$ anti-tag-CAR-expressing cells such as immune cells.
However, the number of anti-tag-CAR-expressing cells such
as immune cells administered to a subject may vary between
wide limits, depending upon the location, source, identity,
extent and severity of the disorder, the age and condition of
the individual to be treated, etc. A physician may ultimately
determine appropriate dosages to be used.

The tagged polypeptides as disclosed herein may be
formulated for administered to a subject using techniques
known to the skilled artisan. Formulations of the tagged
polypeptides may include pharmaceutically acceptable
excipient(s) (carriers or diluents). Excipients included in the
formulations will have different purposes depending, for
example, on the nature of the tag, the antigen binding
domain of the tagged polypeptide, and the mode of admin-
istration. Examples of generally used excipients include,
without limitation: saline, buffered saline, dextrose, water-
for-injection, glycerol, ethanol, and combinations thereof,
stabilizing agents, solubilizing agents and surfactants, buf-
fers and preservatives, tonicity agents, bulking agents, and
lubricating agents.

A formulation of tagged polypeptide may include one
type of tag polypeptide, or more than one type of tagged
polypeptides. The different types of tagged polypeptides
may vary based on the identity of the tag, the antigen binding
moiety of the tagged polypeptide, or a combination thereof.
The tagged polypeptides may be administered to a subject using modes and techniques known to the skilled artisan. Exemplary modes include, but are not limited to, intravenous, intraperitoneal, and intratumoral injection. Other modes include, without limitation, intradermal, subcutaneous (s.c, s.q., sub-Q, Hypo), intramuscular (i.m.), intra-arterial, intramedulary, intracardiac, intra-articular (joint), intrasynovial (joint fluid area), intracranial, intraspinal, and intrathecal (spinal fluids). Formulations comprising the polypeptide are administered to a subject in an amount which is effective for treating the specific indication or disorder. In general, formulations comprising at least about 1 μg/kg to about 100 mg/kg body weight of the tagged polypeptide may be administered to a subject in need of treatment. In most cases, the dosage may be from about 100 μg/kg to about 10 mg/kg body weight of the tagged polypeptide daily, taking into account the routes of administration, symptoms, etc. The amount of tagged polypeptide in formulations administered to a subject may vary between wide limits, depending upon the location, source, identity, extent and severity of the disorder, the age and condition of the individual to be treated, etc. A physician may ultimately determine appropriate dosages to be used.

The timing between the administration of the CAR expressing cell formulation and the tag polypeptide-formulation may range widely depending on factors that include the type of (immune) cells being used, the binding specificity of the CAR, the identity of the tag, the antigen binding moiety of the tagged polypeptide, the identity of the target cell, e.g. cancer cell to be treated, the location of the target cell in the subject, the means used to administer the formulations to the subject, and the health, age and weight of the subject being treated. Indeed, the tagged polypeptide formulation may be administered prior to, simultaneous with, or after the genetically engineered (immune) cell formulation.

Depending on the disorder being treatment the step of administering the CAR expressing cell formulation, or the step of administering the tagged polypeptide formulation, or both, can be repeated one or more times. When two or more formulations of tagged polypeptides may be applied to a subject, the formulations applied may comprise the same or different tagged polypeptides. When two or more formulations of engineered cells such as immune cells expressing the CAR of the invention are applied to a subject, the engineered cells may be of the same cell type or of different cell types, e.g. T cells and/or NK cells. A formulation of cells such as immune cells may also comprise more than one cell type, e.g. subtypes of T cells, each expressing the CAR as disclosed herein.

In another embodiment, said first composition comprising T cells expressing the CAR under an inducible expression system that directly binds to the antigen of said malignant cells as disclosed herein may be for use in the treatment in a subject suffering from cancer/malignancy, i.e. having said malignant cells. Then the second composition comprises said induction agent. The preparation and application of said first and second compositions may be done as described in the preceding embodiment, merely replacing the said first and said second compositions, respectively.

The methods, the combinations of compositions and the (pharmaceutical) compositions of the present invention and as disclosed herein may comprise any embodiment of the invention and/or step as described herein in any order and/or combination resulting in functional methods for the reduction of efficiency of transducing malignant cells and/or the generation of a population of genetically modified T cells and/or the combinations of compositions as disclosed herein.

All definitions, characteristics and embodiments defined herein with regard to the first aspect of the invention as disclosed herein also apply mutatis mutandis in the context of the other aspects of the invention as disclosed herein.

Definitions

Unless defined otherwise, technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the method or composition, yet open to the inclusion of unspecified elements, whether essential or not.

Retroviridae is virus family with a single-stranded, diploid, positive-sense RNA genome that is reverse-transcribed into a DNA intermediate that is then incorporated into the host cell genome. Retroviridae-derived viruses are enveloped particles with a diameter of 80-120 nm.

(Retro-/lenti-/gammaretro-) viral vectors or viral vector particles are replication-deficient viral particles that are derived from the corresponding virus family. They contain Gag and Pol proteins, a single-stranded RNA genome and are usually pseudotyped with heterologous envelope proteins derived from other viruses. The RNA genome of said viral vectors do not contain any viral gene to produce viral progeny, but psi elements and LTRs that are required for efficient packing and reverse transcription in DNA. The DNA intermediate may contain a gene of interest under the control of a suitable promoter, for example, the CMV promoter and the gene of interest is expressed upon integration of said DNA into the genome of the host cell. The process of entering the host cell, delivering the RNA genome, integration and expression of the gene of interest is called transduction. The minimal requirements of a gammaretrovirus or lentivirus based viral vector has been well-described in the art.

*Lentivirus* is a genus of Retroviridae that cause chronic and deadly diseases characterized by long incubation periods, in the human and other mammalian species. The best known lentivirus is the Human Immunodeficiency Virus HIV which can efficiently infect nondividing cells, so lentiviral derived retroviral vectors are one of the most efficient methods of gene delivery.

*Gammaretroviridae* is a genus of the Retroviridae family. Representative species are the murine leukemia virus and the feline leukemia virus.

Paramyxoviridae is a family of viruses in the order of Mononegavirales. There are currently 49 species in this family, divided among 7 genera. Diseases associated with this virus family include measles, mumps, and respiratory tract infections. Members of this virus family are enveloped viruses with a non-segmented, negative-strand RNA genome of about 16 kb. Two membrane proteins with two distinct functions appear as spikes on the virion surface. The H/HN/G proteins mediate binding to the receptor at the cell surface. Upon binding the F proteins induce fusion of the viral envelope and target cell membrane and release of the viral nucleic acid into the cytoplasm.

The term "pseudotyping" or "pseudotyped" as used herein refers to a vector particle bearing envelope glycoproteins derived from other enveloped viruses. Said envelope protein may be selected from the group consisting of BaEV env, VSV-G, RD114-TR, GALV-TR, MV-H/F, NiV-G/F, and Ampho-MLV env.

The term "tropism" as used herein refers to the host range of retroviral or lentiviral vector particles and the ability of retroviral or lentiviral vector particles to transduce cells or cell types of interest of a host. The tropism can be expanded or altered by the envelope protein used for pseudotyping. As used herein, the specificity of the CAR that is displayed on the surface of lentiviral vector particles may also alter the tropism of retroviral or lentiviral vector particles although the CAR protein is not considered as an envelope protein.

The Baboon endogenous retrovirus or BaEV is a type C retrovirus present in multiple proviral copies in the DNA of baboons. In WO2013045639A1 the wild-type BaEV envelope glycoprotein (non-modified BaEV envelope glycoprotein) and BaEV envelope glycoproteins having defined mutations (modifications) that were incorporated at a higher level on the lentiviral surface than the wild-type BaEV glycoprotein are described in detail.

The term "BaEV envelope glycoprotein" or "BaEV env" as used herein refers to the wild-type form of the BaEV envelope glycoprotein or to a mutant of said wild-type BaEV envelope glycoprotein which is at least 80%, at least 85%, at least 90%, at least 95%, or at least 99% identical to said wild-type BaEV envelope glycoprotein, provided that said mutant glycoprotein retains the capacity of the wild-type glycoprotein of binding to and fusing with hematopoietic cells membrane.

The Vesicular Stomatitis Virus (VSV) is a species of the genus *Vesiculovirus* within the family Rhabdoviridae within the order Mononegavirales. The genome of VSV encodes for the G protein that is responsible for binding and entry of the virus into the target cell. It is a homotrimer that induces clathrin-mediated endocytosis in the endosome once the receptor has been bound on the cell surface. In the endosome, the pH shift induces a conformational change of the homotrimer inducing irreversible fusion of the viral envelope and cellular membrane.

Ampho or Amphotropic MLV (4070A) is the amphotropic clone 4070 of the murine leukemia virus (MLV), which is type C gamma retrovirus.

The term "Ampho-MLV env" as used herein refers to the envelope protein of the amphotropic clone 4070A of the murine leukemia virus. The envelope protein may be used for pseudotyping of lentiviral vectors.

The term "RD114" as used herein refers to the wild-type form of the envelope protein of the feline endogenous virus RD114.

The term "RD114-TR" as used herein refers to a chimeric envelope protein, wherein the extracellular and transmembrane part is derived the feline endogenous virus RD114 and the cytoplasmatic part is derived from the cytoplasmatic part of the envelope protein of the Ampho MLV (4070A). The chimeric envelope protein may be used for pseudotyping of lentiviral vectors. The term "GALV" as used herein refers to the wild-type form of the envelope protein of the gibbon ape leukemia virus (GaLV).

The term "GALV-TR" as used herein refers to a chimeric envelope protein, wherein the extracellular and transmembrane part is derived the gibbon ape leukemia virus (GALV) and the cytoplasmatic part is derived from the cytoplasmatic part of the envelope protein of the amphotropic MLV (4070A). The chimeric envelope protein may be used for pseudotyping of lentiviral vectors.

The term "MV-H/F" as used herein refers to the envelope protein H and F of the measles virus that may be used for pseudotyping of lentiviral vectors. The cytoplasmatic portion of the F and H protein may be present in its wildtype form or modified. Such modifications include the addition, deletion or substitution of at least one amino acid residue to enable pseudotyping. U.S. Pat. No. 9,862,971 describes the amino acid modifications of the measles virus envelope proteins that are necessary to pseudotype lentiviral vectors. The tropism of lentiviral vectors pseudotyped with MV-H/F is determined by the H protein. For the H and F protein, the extracellular domain of wildtype or vaccine strains may be used. The H protein may be a chimeric protein that does not interact with its natural receptors (e.g. CD46, SLAM, Nectin-4) and further has at its ectodomain a polypeptide comprising an antigen binding domain.

The term "NIV-G/F" as used herein refers to the envelope protein G and F of the Nipah virus that may be used for pseudotyping of lentiviral vectors. The cytoplasmatic portion of the F and G protein may be present in its wildtype form or modified. Such modifications include the addition, deletion or substitution of at least one amino acid residue Amino acid modifications of the nipah virus envelope proteins are described that are necessary to pseudotype lentiviral vectors (Bender et al., 2016). The tropism of lentiviral vectors pseudotyped with NIV-G/F is determined by the G protein. The G protein may be a chimeric protein that does not interact with its natural receptors and further has at its ectodomain a polypeptide comprising an antigen binding domain.

Target cells in the context of transduction may be cells to be intended to be transduced by a lentiviral vector particle, i.e. herein normally T cells are target cells. Target cells in the context of a CAR T cell therapy may be malignant cells.

The term "LV dose", MOI" or "multiplicity of infection", as used in the present application, refers to the number of transducing lentiviral vectors per cell used for the transduction. The number of transducing LV particles (i.e. the LV titer) is typically determined by applying different volumes of LV containing supernatant to primary cells or cells of a susceptible cell line under standardized conditions. After several days of cultivation and when steady-state levels of the transgene are usually observed the ratio of transgene positive cells (i.e. the transduction efficiency) is determined by flow cytometry or PCR based methods. The LV titer of a given sample can be calculated when the applied volume used for the transduction, the number of seeded cells and the transduction efficiency is taken into account.

For example, a MOI of 1 corresponds to 100 lentiviral vector particles added to a sample containing 100 target cells. A MOI of 5 corresponds to 500 lentiviral vector particles added to a sample containing 100 target cells.

The term "activation" as used herein refers to inducing physiological changes with a cell that increase target cell function, proliferation and/or differentiation.

To generate retroviral vectors particles the gag, pol and env proteins needed to assemble the vector particle are provided in trans by means of a packaging cell line, for example, HEK-293T. This is usually accomplished by transfection of the packaging cell line with one or more plasmids containing the gag, pol and env genes. For the generation of pseudotyped vectors, the env gene, originally derived from the same retrovirus as the gag and pol genes and as the RNA molecule or expression vector, is exchanged for the envelope protein(s) of a different enveloped virus.

The term "transduction" or "transducing" as used herein refers to the genetic modification of cells by retroviral vectors particles encoding (therapeutic) transgenes, such that the retroviral vector binds to the cell, releases the capsid into the cytoplasm, enters the nucleus and the reverse-transcribed retroviral vector genome comprising the transgene is stably integrated into the host cell genome and subsequently expressed by the transduced cell.

The terms "Psi positive" and "psi negative", as used in the present application, refer to a nucleic acid molecule where the retroviral psi element is present and absent, respectively. The psi element is a cis-acting signal located near the 5' end of the retroviral genome and designates a packaging signal, which is of importance during assembly of the viruses and leads to the incorporation of the viral RNA into the viral core. Thus, a psi negative RNA does not comprise the retroviral psi element and consequently will not be assembled into a vector particle of the present invention; in contrast, a psi positive RNA that does comprise said psi element will be effectively assembled into the vector particle.

Thus, an exemplary pseudotyped vector particle based on the HIV-1 retrovirus comprises the (1) HIV-1 Gag and Pol proteins, (2) an RNA molecule derived from the HIV-1 genome that may be used to generate a retroviral vector particle based on the HIV-1 genome lacking the gag, env, pol, tat, vif, vpr, vpu and nef genes, but still comprising the LTRs, the psi element and a CMV promoter followed by the gene to be transduced, for example, a gene for the CAR protein, and (3) the envelope protein used for pseudotyping, for example, VSV-G.

The terms "cells of the blood system of a subject" or "cells of the circulatory system of a subject" or "cells of the blood of a subject" can be used interchangeably and mean all cells that circulate in the cardiovascular system of a subject, including red blood cells and white bold cells.

The "circulatory system" is an organ system of a subject that permits blood to circulate and transport nutrients (such as amino acids and electrolytes), oxygen, carbon dioxide, hormones, and blood cells to and from the cells in the body to provide nourishment and help in fighting diseases, stabilize temperature and pH, and maintain homeostasis. The circulatory system comprises two separate systems: the cardiovascular system, which distributes blood, and the lymphatic system, which circulates lymph.

The term "malignant cells of the blood system of a subject that are not derived from T cells" as used herein refers to malignant cells of the blood system that may circulate in the cardiovascular system of a subject excluding malignant cells that originate from T cells and/or T cell progenitors. Examples for cells of the blood system of a subject that are not derived from T cells may be circulating tumor cells (i.e. cells that are shed from a primary tumor; CTCs), malignant B cells, malignant B cell subsets, malignant B cell progenitors, malignant NK cells, malignant stem cells, malignant myeloid cells, malignant myeloid subsets or malignant myeloid progenitors.

The term "incubation of the cells of said sample with said lentiviral vector particle" means contacting the lentiviral vector particles to the sample comprising T cells and said malignant cells for a period of time. During this contacting preferentially the T cells are transduced with said lentiviral vector particles.

The term "wherein the efficiency of transducing said malignant cells induced by said incubation is reduced compared to the efficiency of transducing said malignant cells of said sample comprising T cells and said malignant cells wherein said lentiviral vector particles are replaced by lentiviral vector particles comprising a nucleic acid encoding a CAR, wherein said CAR has an antigen binding domain specific for an antigen that is expressed on the surface of said malignant cells, thereby generating lentiviral vector particles comprising said CAR that has an antigen binding domain specific for an antigen that is expressed on the surface of said malignant cells" means that two transduction processes are performed and compared with regard to their efficiency of transducing said malignant cells. The first transduction process is with the lentiviral vector particles comprising a nucleic acid encoding a chimeric antigen receptor (CAR), wherein the antigen binding domain of said CAR binds to a tag of a tagged polypeptide, wherein said polypeptide binds to an antigen expressed on the surface of said malignant cells. And the second transduction process is performed under the same (identical) conditions (e.g. the same LV dose) but with replacement of the lentiviral vector particles by lentiviral vector particles comprising a CAR that has an antigen binding domain specific for an antigen that is expressed on the surface of said malignant cells.

The term "wherein the efficiency of transducing said malignant cells induced by said incubation is reduced compared to the efficiency of transducing said malignant cells of said sample comprising T cells and said malignant cells wherein said lentiviral vector particles are replaced by lentiviral vector particles that do not comprise said gene expression system thereby generating lentiviral vector particles comprising said CAR that has an antigen binding domain specific for an antigen that is expressed on the surface of said malignant cells" means that two transduction processes are performed and compared with regard to their efficiency of transducing said malignant cells. The first transduction process is with the lentiviral vector particles comprising a nucleic acid encoding a chimeric antigen receptor (CAR) and a gene expression system, wherein said CAR is expressed under the control of said gene expression system allowing the expression of said CAR in the transduced cells but said CAR is not displayed in the LV packaging cells and thereby not displayed on the lentiviral vector particles, wherein said CAR has an antigen binding domain that binds to an antigen that is expressed on the surface of said malignant cells. And the second transduction process is performed under the same (identical) conditions but with replacement of the lentiviral vector particles by lentiviral vector particles comprising said CAR but that do not comprise said gene expression system.

The steps of the method as disclosed herein comprising a) "providing said sample comprising T cells and said malignant cells" (or "a sample provided that comprises T cells and said malignant cells"), and b) "incubation of the cells of said sample with said lentiviral vector particles" may also be summarized as step: "incubation of said lentiviral vector particles with the cells of said sample comprising T cells and said malignant cells".

The terms "a combination of compositions comprising a first component and a second component" or "a set comprising a first component and a second component" or "a system comprising a first component and a second component" or "a kit comprising a first component and a second component" as used herein may be used interchangeably. The term "combination of compositions comprising a first component and a second component" as used herein refers to two compositions that exist originally separated from each other, but can be combined, and when combined preferentially exert on effect that is not observed in the separated components alone. The combination of both components or portions thereof to one comprehensive composition may take place at any time defined e.g. by an operator. The adding of the first component to the second component or vice versa may occur directly or indirectly. Indirectly here may mean, e.g. the addition of both components separately to another composition or liquid such as into the blood of a subject. In some instances, a third composition may be part of the combinations of compositions as disclosed herein and may be added to the first and second composition, normally after the second composition has been added to the first composition, in order to exert the effects associated with the third composition as disclosed herein.

The term "anti-tumoral activities" as used herein refers to any cellular function of CAR expressing cells that are induced upon binding (direct or indirectly) of said CAR to malignant cells expressing a tumor antigen. EVTL Such cellular functions induced upon binding of said CAR expressing T cells to said malignant cells are well described in the art EVTL and may comprise T cell activation, expression of T cell activation markers, differentiation, cell cycle progression, proliferation, expression and release of cytokines, exhaustion, cytotoxicity, lysis of malignant cells.

The modulatory agents may be selected from the group consisting of agonistic antibodies or antigen binding fragment thereof, cytokines, recombinant costimulatory molecules and small drug inhibitors. Said modulatory agents are anti-CD3 and anti-CD28 antibodies or fragments thereof coupled to beads or nanostructures. The modulatory agents may be a nanomatrix, the nanomatrix comprising a) a matrix of mobile polymer chains, and b) attached to said matrix of mobile polymer chains anti-CD3 and anti-CD28 antibodies or fragments thereof, wherein the nanomatrix is 1 to 500 nm in size. The anti-CD3 and anti-CD28 antibodies or fragments thereof may be attached to the same or to separate matrices of mobile polymer chains. If the anti-CD3 and anti-CD28 antibodies or fragments thereof are attached to separate matrices of mobile polymer chains, fine-tuning of nanomatrices for the stimulation of the T cells is possible. The nanomatrix may be biodegradable. The nanomatrix may be of collagen, purified proteins, purified peptides, polysaccharides, glycosaminoglycans, or extracellular matrix compositions. A polysaccharide may include for example, cellulose ethers, starch, gum arabic, agarose, dextran, chitosan, hyaluronic acid, pectins, xanthan, guar gum or alginate. The choice of degrading enzyme agent will be determined by the glycosidic linkage. Where the macromolecular coating is a polysaccharide, the polysaccharide will be chosen to have glycosidic linkages not normally found in mammalian cells. Hydrolases that recognize specific glycosidic structures may be used as an enzyme e.g. dextran and dextranase, which cleaves at the $\alpha(1\rightarrow6)$ linkage; cellulose and cellulase, which cleaves at the $\beta(1\rightarrow4)$ linkage; amylose and amylase; pectin and pectinase; chitin and chitinase, etc.

The term "depletion" as used herein refers to a process of a negative selection that separates the desired cells from the undesired cells, herein normally the malignant cells, which are labelled by an antibody or antigen-binding fragment thereof coupled to a solid phase such as a particle, fluorophore or hapten.

The term "particle" outside the field of "viral vector particle" as used herein refers to a solid phase such as colloidal particles, microspheres, nanoparticles, or beads. Methods for generation of such particles are well known in the field of the art. The particles may be magnetic particles. The particles may be in a solution or suspension or they may be in a lyophilised state prior to use in the present invention. The lyophilized particle is then reconstituted in convenient buffer before contacting the sample to be processed regarding the present invention The term "magnetic" in "magnetic particle" as used herein refers to all subtypes of magnetic particles which can be prepared with methods well known to the skilled person in the art, especially ferromagnetic particles, superparamagnetic particles and paramagnetic particles. "Ferromagnetic" materials are strongly susceptible to magnetic fields and are capable of retaining magnetic properties when the field is removed. "Paramagnetic" materials have only a weak magnetic susceptibility and when the field is removed quickly lose their weak magnetism. "Superparamagnetic" materials are highly magnetically susceptible, i.e. they become strongly magnetic when placed in a magnetic field, but, like paramagnetic materials, rapidly lose their magnetism.

The linkage between antibody (or an antigen binding fragment thereof) and particle can be covalent or non-covalent. A covalent linkage can be, e.g. the linkage to carboxyl-groups on polystyrene beads, or to $NH_2$ or $SH_2$ groups on modified beads. A non-covalent linkage is e.g. via biotin-avidin or a fluorophore-coupled-particle linked to anti-fluorophore antibody. Methods for coupling antibodies to particles, fluorophores, haptens like biotin or larger surfaces such as culture dishes are well known to the skilled person in the art.

For enrichment, isolation or selection in principle any sorting technology can be used. This includes for example affinity chromatography or any other antibody-dependent separation technique known in the art. Any ligand-dependent separation technique known in the art may be used in conjunction with both positive and negative separation techniques that rely on the physical properties of the cells. An especially potent sorting technology is magnetic cell sorting. Methods to separate cells magnetically are commercially available e.g. from Invitrogen, Stem cell Technologies, in Cellpro, Seattle or Advanced Magnetics, Boston. For example, monoclonal antibodies can be directly coupled to magnetic polystyrene particles like Dynal M 450 or similar magnetic particles and used e.g. for cell separation. The Dynabeads technology is not column based, instead these magnetic beads with attached cells enjoy liquid phase kinetics in a sample tube, and the cells are isolated by placing the tube on a magnetic rack. However, in a preferred embodiment for enriching CD4+ and/or CD8+ T cells from a sample comprising T cells according the present invention monoclonal antibodies or antigen binding fragments thereof are used in conjunction with colloidal superparamagnetic microparticles having an organic coating by e.g. polysaccharides (Magnetic-activated cell sorting (MACS) technology (Miltenyi Biotec, Bergisch Gladbach, Germany)). These particles (nanobeads or MicroBeads) can be either directly conjugated to monoclonal antibodies or used in combination with anti-immunoglobulin, avidin or anti-hapten-specific MicroBeads.

The MACS technology allows cells to be separated by incubating them with magnetic nanoparticles coated with antibodies directed against a particular surface antigen. This causes the cells expressing this antigen to attach to the magnetic nanoparticles. Afterwards the cell solution is transferred on a column placed in a strong magnetic field. In this step, the cells attach to the nanoparticles (expressing the antigen) and stay on the column, while other cells (not expressing the antigen) flow through. With this method, the cells can be separated positively or negatively with respect to the particular antigen(s)/marker(s).

In case of a positive selection the cells expressing the antigen(s) of interest, which attached to the magnetic column, are washed out to a separate vessel, after removing the column from the magnetic field.

In case of a negative selection the antibody used is directed against surface antigen(s) which are known to be present on cells that are not of interest. After application of the cells/magnetic nanoparticles solution onto the column the cells expressing these antigens bind to the column and the fraction that goes through is collected, as it contains the cells of interest. As these cells are non-labelled by an antibody coupled to nanoparticels, they are "untouched".

The procedure can be performed using direct magnetic labelling or indirect magnetic labelling. For direct labelling the specific antibody is directly coupled to the magnetic particle. Indirect labelling is a convenient alternative when direct magnetic labelling is not possible or not desired. A primary antibody, a specific monoclonal or polyclonal antibody, a combination of primary antibodies, directed against any cell surface marker can be used for this labelling strategy. The primary antibody can either be unconjugated, biotinylated, or fluorophore-conjugated. The magnetic labelling is then achieved with anti-immunoglobulin MicroBeads, anti-biotin MicroBeads, or anti-fluorophore MicroBeads.

The term "disruption" as used herein in the context of disruption of a magnetic particle or modulatory agent for activation may refer to the removal by washing alone and/or by adding a competing agent and subsequent washing and/or by chemical disruption, i.e. by adding a substance (non-proteinous, chemical compound) that breaks covalent bonds and/or by enzymatic disruption and subsequent washing, and/or by input of energy (physical disruption) that breaks covalent bonds.

The term "competitive reaction" in the context of disruption as used herein refers to a magnetic particle or modulatory agent for activation that comprise 2 components, that are not covalently linked wherein one component binds to said cell via antibodies or antigen binding fragments specific for CD3, CD28, CD4 and/or CD28 and contains a tag and a second component that binds to said tag and wherein said binding to so said tag may be dissolved by the addition of a competitor. The competitor may compete and/or replace one component, said magnetic particle, said modulatory agent or said antibodies or antigen binding fragments thereof for example due to higher affinity to the respective component or due to higher concentration of the competitor molecule compared to concentration of the magnetic particle or modulatory agent that is indirectly coupled to antibodies or antigen binding fragments thereof specific for CD3, CD28, CD4 and/or CD8.

The term "enzymatical disruption" as used herein in the context of disruption of magnetic particles or modulatory agents refers to antibodies or antigen binding fragments thereof specific for CD3, CD28, CD4 or CD8 that are directly or indirectly linked via a biodegradable linker and wherein said biodegradable linker may be specifically biodegraded, digested or cut by the activity of said enzyme and thereby split said magnetic particle or modulatory agent in at least two separate molecules. Released single antibody or antigen binding fragment thereof such as a Fab specific for CD3 or CD28 then has no further effect on activation of the T cell to which it is bound. In addition, if said antibody or antigen binding fragment thereof such as said Fab has low affinity and/or a high k(off) rate said antibody or antigen binding fragment thereof such as said Fab will be removed from the cell to that is has bound.

The term "chemical disruption" as used herein in the context of disruption of magnetic particles or modulatory agents refers to antibodies or antigen binding fragments thereof specific for CD3, CD28, CD4 or CD8 that are directly or indirectly linked via a chemically degradable linker and wherein said chemically degradable linker may be specifically degraded or cleaved by the addition of a non-proteinous, chemical substance that breaks covalent bonds under physiological conditions and thereby split said magnetic particle or modulatory agent in at least two separate molecules. Examples for suitable reactions for chemical disruption under physiological conditions may be reductions, such as the reduction of disulfide bonds by a reducing agent or the reduction of diazo bonds with dithionite, or oxidations, such as the cleavage of glycol residues by periodate.

Released single antibody or antigen binding fragment thereof such as a Fab specific for CD3 or CD28 then has no further effect on activation of the T cell to which it is bound. In addition, if said antibody or antigen binding fragment thereof such as said Fab has low affinity and/or a high k(off) rate said antibody or antigen binding fragment thereof such as said Fab will be removed from the cell to that is has bound.

The term "physical disruption" as used herein in the context of disruption of magnetic particles or modulatory agents refers to antibodies or antigen binding fragments thereof specific for CD3, CD28, CD4 or CD8 that are directly or indirectly linked via a physically disruptable linker and wherein said physically disruptable linker may be specifically degraded or cleaved by energy input that breaks covalent bonds under physiological conditions and thereby split said magnetic particle or modulatory agent in at least two separate molecules. Examples for suitable reactions for physical disruption under physiological conditions may be photo-reactions, such as the photocleavage of light sensitive linkers by UV or visible light as exemplified by the cleavage of ortho-nitrobenzyl derivatives by near-UV light (300-365 nm). Released single antibody or antigen binding fragment thereof such as a Fab specific for CD3 or CD28 then has no further effect on activation of the T cell to which it is bound. In addition, if said antibody or antigen binding fragment thereof such as said Fab has low affinity and/or a high k(off) rate said antibody or antigen binding fragment thereof such as said Fab will be removed from the cell to that is has bound.

In general, a CAR may comprise an extracellular domain (extracellular part) comprising the antigen binding domain, a transmembrane domain and a cytoplasmic signaling domain (intracellular signaling domain). The extracellular domain may be linked to the transmembrane domain by a linker or spacer. The extracellular domain may also comprise a signal peptide. In some embodiments of the invention the antigen binding domain of a CAR binds a tag or hapten that is coupled to a polypeptide ("haptenylated" or "tagged" polypeptide), wherein the polypeptide may bind to a disease-associated antigen such as a tumor associated antigen (TAA) that may be expressed on the surface of a cancer cell.

Such a CAR may be also referred to as "anti-tag" CAR or "adapterCAR" or "Adapter-CAR" or "universal CAR" as disclosed e.g. in U.S. Pat. No. 9,233,125B2.

The haptens or tags may be coupled directly or indirectly to a polypeptide (the tagged polypeptide), wherein the polypeptide may bind to said disease associated antigen expressed on the (cell) surface of a target. The tag may be e.g. dextran or a hapten such as biotin or fluorescein isothiocyanate (FITC) or phycoerythrin (PE), but the tag may also be a peptide sequence e.g. chemically or recombinantly coupled to the polypeptide part of the tagged polypeptide. The tag may also be streptavidin. The tag portion of the tagged polypeptide is only constrained by being a molecular that can be recognized and specifically bound by the antigen binding domain specific for the tag of the CAR. For example, when the tag is FITC (Fluorescein isothiocyanate), the tag-binding domain may constitute an anti-FITC scFv. Alternatively, when the tag is biotin or PE (phycoerythrin), the tag-binding domain may constitute an anti-biotin scFv or an anti-PE scFv.

A "signal peptide" refers to a peptide sequence that directs the transport and localization of the protein within a cell, e.g. to a certain cell organelle (such as the endoplasmic reticulum) and/or the cell surface.

Generally, an "antigen binding domain" refers to the region of the CAR that specifically binds to an antigen, e.g. to a tumor associated antigen (TAA) or tumor specific antigen (TSA). The CARs of the invention may comprise one or more antigen binding domains (e.g. a tandem CAR). Generally, the targeting regions on the CAR are extracellular. The antigen binding domain may comprise an antibody or an antigen binding fragment thereof. The antigen binding domain may comprise, for example, full length heavy chain, Fab fragments, single chain Fv (scFv) fragments, divalent single chain antibodies or diabodies. Any molecule that binds specifically to a given antigen such as affibodies or ligand binding domains from naturally occurring receptors may be used as an antigen binding domain. Often the antigen binding domain is a scFv. Normally, in a scFv the variable regions of an immunoglobulin heavy chain and light chain are fused by a flexible linker to form a scFv. Such a linker may be for example the "$(G_4/S)_3$-linker".

In some instances, it is beneficial for the antigen binding domain to be derived from the same species in which the CAR will be used in. For example, when it is planned to use it therapeutically in humans, it may be beneficial for the antigen binding domain of the CAR to comprise a human or humanized antibody or antigen binding fragment thereof. Human or humanized antibodies or antigen binding fragments thereof can be made by a variety of methods well known in the art.

"Spacer" or "hinge" as used herein refers to the hydrophilic region which is between the antigen binding domain and the transmembrane domain. The CARs of the invention may comprise an extracellular spacer domain but is it also possible to leave out such a spacer. The spacer may include e.g. Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8alpha hinge.

The transmembrane domain of the CAR may be derived from any desired natural or synthetic source for such domain. When the source is natural the domain may be derived from any membrane-bound or transmembrane protein. The transmembrane domain may be derived for example from CD8alpha or CD28. When the key signaling and antigen recognition modules (domains) are on two (or even more) polypeptides then the CAR may have two (or more) transmembrane domains. The splitting key signaling and antigen recognition modules enable for a small molecule-dependent, titratable and reversible control over CAR cell expression (e.g. WO2014127261A1) due to small molecule-dependent heterodimerizing domains in each polypeptide of the CAR.

The cytoplasmic signaling domain (or the intracellular signaling domain) of the CAR is responsible for activation of at least one of the normal effector functions of the immune cell in which the CAR is expressed. "Effector function" means a specialized function of a cell, e.g. in a T cell an effector function may be cytolytic activity or helper activity including the secretion of cytokines. The intracellular signaling domain refers to the part of a protein which transduces the effector function signal and directs the cell expressing the CAR to perform a specialized function. The intracellular signaling domain may include any complete, mutated or truncated part of the intracellular signaling domain of a given protein sufficient to transduce a signal which initiates or blocks immune cell effector functions.

Prominent examples of intracellular signaling domains for use in the CARs include the cytoplasmic signaling sequences of the T cell receptor (TCR) and co-receptors that initiate signal transduction following antigen receptor engagement.

Generally, T cell activation can be mediated by two distinct classes of cytoplasmic signaling sequences, firstly those that initiate antigen-dependent primary activation through the TCR (primary cytoplasmic signaling sequences, primary cytoplasmic signaling domain) and secondly those that act in an antigen-independent manner to provide a secondary or co-stimulatory signal (secondary cytoplasmic signaling sequences, co-stimulatory signaling domain). Therefore, an intracellular signaling domain of a CAR may comprise one or more primary cytoplasmic signaling domains and/or one or more secondary cytoplasmic signaling domains.

Primary cytoplasmic signaling domains that act in a stimulatory manner may contain ITAMs (immunoreceptor tyrosine-based activation motifs).

Examples of ITAM containing primary cytoplasmic signaling domains often used in CARs are that those derived from TCRζ (CD3ζ), FcRgamma, FcRbeta, CD3gamma, CD3delta, CD3epsilon, CD5, CD22, CD79a, CD79b, and CD66d. Most prominent is sequence derived from CD3ζ.

The cytoplasmic domain of the CAR may be designed to comprise the CD3ζ signaling domain by itself or combined with any other desired cytoplasmic domain(s). The cytoplasmic domain of the CAR can comprise a CD3ζ chain portion and a co-stimulatory signaling region (domain). The co-stimulatory signaling region refers to a part of the CAR comprising the intracellular domain of a co-stimulatory molecule. A co-stimulatory molecule is a cell surface molecule other than an antigen receptor or their ligands that is required for an efficient response of lymphocytes to an antigen. Examples for a co-stimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

The cytoplasmic signaling sequences within the cytoplasmic signaling part of the CAR may be linked to each other with or without a linker in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3ζ and the signaling domain of CD28. In another example the cytoplasmic domain may comprise the signaling domain of CD3ζ and the signaling domain of CD137. In a further example, the cytoplasmic domain may comprise the signaling domain of CD3ζ, the signaling domain of CD28, and the signaling domain of CD137.

As aforementioned either the extracellular part or the transmembrane domain or the cytoplasmic domain of a CAR may also comprise a heterodimerizing domain for the aim of splitting key signaling and antigen recognition modules of the CAR.

The CAR may be further modified to include on the level of the nucleic acid encoding the CAR one or more operative elements to eliminate CAR expressing immune cells by virtue of a suicide switch. The suicide switch can include, for example, an apoptosis inducing signaling cascade or a drug that induces cell death. In one embodiment, the nucleic acid expressing and encoding the CAR can be further modified to express an enzyme such thymidine kinase (TK) or cytosine deaminase (CD). The CAR may also be part of a gene expression system that allows controlled expression of the CAR in the immune cell. Such a gene expression system may be an inducible gene expression system and wherein when an induction agent is administered to a cell being transduced with said inducible gene expression system, the gene expression system is induced and said CAR is expressed on the surface of said transduced cell.

In some embodiments, the endodomain may contain a primary cytoplasmic signaling domains or a co-stimulatory region, but not both. In these embodiments, an immune effector cell containing the disclosed CAR is only activated if another CAR containing the missing domain also binds its respective antigen.

In some embodiment of the invention the CAR may be a "SUPRA" (split, universal, and programmable) CAR, where a "zipCAR" domain may link an intra-cellular costimulatory domain and an extracellular leucine zipper (WO2017/091546). This zipper may be targeted with a complementary zipper fused e.g. to an scFv region to render the SUPRA CAR T cell tumor specific. This approach would be particularly useful for generating universal CAR T cells for various tumors; adaptor molecules could be designed for tumor specificity and would provide options for altering specificity post-adoptive transfer, key for situations of selection pressure and antigen escape.

In some embodiments, in a second CAR of an immune cell expressing a first and a second CAR the cytoplasmic signaling domain of the second CAR may comprise a ligation-off inhibitory domain. When the second antigen binds to the second CAR then the ligation-off inhibitory domain becomes inactive and allows the activation of the cytoplasmic signaling domain of the first CAR, when the first antigen binds to the first CAR. Said ligation-off inhibitory domain of said second CAR may comprise all or part of the endodomain from CD148 or CD45.

In some embodiments, in a second CAR of an immune cell expressing a first and a second CAR the cytoplasmic signaling domain of the second CAR may comprise a ligation-on inhibitory domain. When the second antigen binds to the second CAR then the ligation-on inhibitory domain becomes active and inhibits the cytoplasmic signaling domain of the first CAR, when the first antigen binds to the first CAR. Said ligation-on inhibitory domain of said second CAR may be cytoplasmic signaling domain comprising at least one signal transduction element that inhibits an effector immune cell. Such an inhibitory signal transduction element may be an immune checkpoint protein, such an immune checkpoint protein may be e.g. PD1; CTLA4; BTLA; 2B4; CD 160; CEACAM, such as CEACAM1; or KIRs.

The CARs of the present invention may be designed to comprise any portion or part of the above-mentioned domains as described herein in any order and/or combination resulting in a functional CAR, i.e. a CAR that mediated an immune effector response of the immune effector cell that expresses the CAR as disclosed herein.

The term "antigen expressed on the surface of a (target) cell" or "cell (surface) marker", as used in the present invention, refers to a molecule present on the surface of a cell, preferentially on a target cell. Such molecules can be, inter alia, peptides or proteins that may comprise sugar chains or lipids, clusters of differentiation (CDs), antibodies or receptors. Since not all populations of cells express the same cell markers, a cell marker can thus be used to identify, select or isolate a given population of cells expressing a specific cell marker. As an example, CD4 is a cell marker expressed by T helper cells, regulatory T cells, and dendritic cells. Thus, T helper cells, regulatory T cells, and dendritic cells can be identified, selected or otherwise isolated, inter alia by a FACS cell sorter, by means of the CD4 cell marker.

The term "tagged polypeptide" as used herein refers to a polypeptide that has bound thereto directly or indirectly at least one additional component, i.e. the tag. The tagged polypeptide as used herein is able to bind an antigen expressed on a target cell. The polypeptide may be an antibody or antigen binding fragment thereof that binds to an antigen expressed on the surface of a target cell such as a tumor associated antigen on a cancer cell. The polypeptide of the tagged polypeptide alternatively may a cytokine or a growth factor or another soluble polypeptide that is capable of binding to an antigen of a target cell.

The term "adapter" or "adapter molecule" as used herein refers to a tagged polypeptide that can bind to an antigen of a target cell, e.g. antibody or antigen binding fragment thereof, and has bound thereto directly or indirectly at least one additional component, i.e. the tag. The adapter or adapter molecule may by a tagged antibody or antigen binding fragment thereof, a cytokine or a growth factor or another soluble polypeptide that is capable of binding to an antigen of a target cell.

The tag may be e.g. a hapten or dextran and the hapten or dextran may be bound by the antigen binding domain of the polypeptide comprising an antigen binding domain specific for the tag.

Haptens such as e.g. FITC, biotin, PE, streptavidin or dextran are small molecules that elicit an immune response only when attached to a large carrier such as a protein; the carrier may be one that also does not elicit an immune response by itself. Once the body has generated antibodies to a hapten-carrier adduct, the small-molecule hapten may also be able to bind to the antibody, but it will usually not initiate an immune response; usually only the hapten-carrier adduct can do this.

But the tag may also be a peptide sequence e.g. chemically or recombinantly coupled to the polypeptide part of the tagged polypeptide. The peptide may be selected from the group consisting of c-Myc-tag, Strep-Tag, Flag-Tag, and Polyhistidine-tag The tag may also be streptavidin. The tag portion of the tagged polypeptide is only constrained by being a molecular that can be recognized and specifically bound by the antigen binding domain specific for the tag of the CAR. For example, when the tag is FITC (Fluorescein isothiocyanate), the tag-binding domain may constitute an anti-FITC scFv. Alternatively, when the tag is biotin or PE (phycoerythrin), the tag-binding domain may constitute an anti-biotin scFv or an anti-PE scFv.

The term "antibody" as used herein is used in the broadest sense to cover the various forms of antibody structures including but not being limited to monoclonal and polyclonal antibodies (including full length antibodies), multispecific antibodies (e.g. bispecific antibodies), antibody fragments, i.e. antigen binding fragments of an antibody, immunoadhesins and antibody-immunoadhesin chimeras, that specifically recognize (i.e. bind) an antigen. "Antigen binding fragments" comprise a portion of a full-length antibody, preferably the variable domain thereof, or at least the antigen binding site thereof ("an antigen binding fragment of an antibody"). Examples of antigen binding fragments include Fab (fragment antigen binding), scFv (single chain fragment variable), single domain antibodies, diabodies, dsFv, Fab', diabodies, single-chain antibody molecules, and multispecific antibodies formed from antibody fragments.

The terms "having specificity for", "specifically binds" or "specific for" with respect to an antigen-binding domain of an antibody, of a fragment thereof or of a CAR refer to an antigen-binding domain which recognizes and binds to a specific antigen, but does not substantially recognize or bind other molecules in a sample. An antigen-binding domain that binds specifically to an antigen from one species may bind also to that antigen from another species. This cross-species reactivity is not contrary to the definition of that antigen-binding domain as specific. An antigen-binding domain that specifically binds to an antigen may bind also to different allelic forms of the antigen (allelic variants, splice variants, isoforms etc.). This cross reactivity is not contrary to the definition of that antigen-binding domain as specific.

Immunotherapy is a medical term defined as the "treatment of disease by inducing, enhancing, or suppressing an immune response" Immunotherapies designed to elicit or amplify an immune response are classified as activation immunotherapies, while immunotherapies that reduce or suppress are classified as suppression immunotherapies. Cancer immunotherapy as an activating immunotherapy attempts to stimulate the immune system to reject and destroy tumors. Adoptive cell transfer uses cell-based, preferentially T cell-based or NK cell-based cytotoxic responses to attack cancer cells. T cells that have a natural or genetically engineered reactivity to a patient's cancer are generated in-vitro and then transferred back into the cancer patient. Then the immunotherapy is referred to as "CAR immunotherapy" or in case of use of T cells only as "CAR T cell therapy" or "CAR T cell immunotherapy".

The term "treatment" as used herein means to reduce the frequency or severity of at least one sign or symptom of a disease.

The terms "therapeutically effective amount" or "therapeutically effective population" mean an amount of a cell population which provides a therapeutic benefit in a subject.

As used herein, the term "subject" refer to an animal. Preferentially, the subject is a mammal such as mouse, rat, cow, pig, goat, chicken dog, monkey or human More preferentially, the individual is a human. The subject may be a subject suffering from a disease such as cancer (a patient) having malignant cells.

The term "assessing the outcome of a treatment of a malignancy" as used herein refer to the ability of predicting, forecasting or correlating a given detection or measurement with a future outcome associated with response to a CAR T cell therapy treatment in a subject suffering from said malignancy. In this context "a good (or positive) outcome" means that in the in-vitro method for assessing the outcome of the treatment of a malignancy in a subject as disclosed herein the analysis of the antitumoral activities of the transduced T cells reveals the capability of the transduced T cells to lyse at least some of the malignant cells present in the sample to be analyzed.

The term "expression" as used herein is defined as the transcription and/or translation of a particular nucleotide sequence driven by its promoter in a cell.

The term "Tissue Specific Promoter" as used herein refers to a promoter that is active in a specific type of cells or tissues such as B cells, T cells, monocytic cells, leukocytes and macrophages.

The terms "engineered cell" and "genetically modified cell" as used herein can be used interchangeably. The terms mean containing and/or expressing a foreign gene or nucleic acid sequence which in turn modifies the genotype or phenotype of the cell or its progeny. Especially, the terms refer to the fact that cells, preferentially T cells can be manipulated by recombinant methods well known in the art to express stably or transiently peptides or proteins which are not expressed in these cells in the natural state. For example, T cells, preferentially human T cells are engineered to express an artificial construct such as a chimeric antigen receptor on their cell surface. For example, the CAR sequences may be delivered into cells using a retroviral or lentiviral vector. The term "transgene" describes a segment of DNA containing a gene sequence that has been isolated from one organism and is introduced into a different organism. This non-native segment of DNA may either retain the ability to produce RNA or protein in the transgenic organism or alter the normal function of the transgenic organism's genetic code.

The term "tumor" is known medically as a neoplasm. Not all tumors are cancerous; benign tumors do not invade neighboring tissues and do not spread throughout the body.

The term "cancer" is known medically as a malignant neoplasm. Cancer is a broad group of diseases involving unregulated cell growth and includes all kinds of leukemia. In cancer, cells (cancerous cells) divide and grow uncontrollably, forming malignant tumors, and invading nearby parts of the body. The cancer may also spread to more distant parts of the body through the lymphatic system or bloodstream. There are over 200 different known cancers that affect humans. Malignant cells are part of a malignant tumor.

"Malignancy" is a term for diseases in which abnormal cells, i.e. malignant cells" divide without control and can invade nearby tissues. Malignant cells can also spread to other parts of the body through the blood and lymph systems. There are several main types of malignancy. Carcinoma is a malignancy that begins in the skin or in tissues that line or cover internal organs. Sarcoma is a malignancy that begins in bone, cartilage, fat, muscle, blood vessels, or other connective or supportive tissue. Leukemia is a malignancy that starts in blood-forming tissue, such as the bone marrow, and causes large numbers of abnormal blood cells to be produced and enter the blood. Lymphoma and multiple myeloma are malignancies that begin in the cells of the immune system. Central nervous system cancers are malignancies that begin in the tissues of the brain and spinal cord.

EXAMPLES

Example 1: Principle of Binding of Lentiviral Vector Particles to Cells via a Target Specific CAR Protein CAR T cells are usually generated from heterogenous samples such as leukapheresis or isolated human PBMC which contain leukocytes such as T cells, B cells, NK cells etc. The sample may also contain malignant cells. VSV-G pseudotyped lentiviral vectors encoding CARs and LNGFR also display the CAR and LNGFR protein on the surface of lentiviral vector particles. Lentiviral vector particles displaying CARs that are specific for antigens expressed by specific cell types will preferentially bind via the CAR to cells expressing the antigen (FIG. 1C). Lentiviral vector particles displaying CARs that are specific for adapter molecules but not specific for any cellular antigen will bind in the absence of said adapter molecule to cells via VSV-G and the VSV-G receptor LDLR instead (FIG. 1B). Accordingly, lentiviral vector particles encoding for proteins other than CARs or encoding CARs under the control of inducible systems in the absence of the induction reagent will bind via VSV-G to cells expressing the VSV-G receptor LDLR (FIG. 1C).

Example 2: Generation and Titration of VSV-G Pseudotyped Lentiviral Vector Particles Lentiviral vector particles pseudotyped with VSV-G were generated by transient transfection of HEK-293T (FIG. 2,3) cells. Alternatively, HEK-293T cells stably expressing CARs and LNGFR were used (FIG. 4,5) (Example 3). HEK-293T cells seeded in T175 flasks in DMEM/10% FCS (Biowest, Cat. No. 12362; Biochrom, Cat. No. S0415) were transfected with a plasmid encoding for VSV-G, a packaging plasmid encoding gag/pol/rev and a psi-positive transfer vector plasmid encoding for GFP or for CAR (AdapterCAR, CD19-CAR or CD318-CAR). The pseudotyped lentiviral vector particles were harvested 48 h post transfection. To remove cellular debris, the supernatant was collected, centrifuged for 10 min at 1000 rpm, followed by filtration through a 0.45 μm filter. To concentrate, the filtered supernatant was centrifuged for 24 h at 4° C. with 5350×g. The pelleted lentiviral vector particles were resuspended in 250 μl precooled PBS, aliquoted and stored at −80° C. for later use. Pseudotyped lentiviral vector particles were titrated on SupT1 cells. Therefore, 2E5 cells were seeded 150 μl RPMI (5% stable Glutamin) in 96 well round bottom plates. The GFP or CAR encoding vector particles were serially diluted in 50 μl RPMI (5% stable Glutamin) 24 h post transduction 90 μl fresh cultivation medium (RPMI, 5% stable Glutamin, 10% FCS) was added to the cells. 96 h post transduction the transduction efficiency was determined by flow cytometry determining the ratio of GFP or LNGFR positive (α-LNGFR-APC, Miltenyi Biotec, 130-112-602). The ratio of GFP or LNGFR positive cells, the dilution factor and the volume of lentiviral vector particles applied was used to calculate the lentiviral vector titer (i.e. transducing units per volume (TU/ml).

Example 3: Generation of HEK293T Cells Stably Expressing CARs for the Generation of Pseudotyped Lentiviral Vectors Displaying CAR on the Surface and Encoding for GFP or Delivering GFP as Protein 3.5E5 HEK293T cells were seeded in cultivation medium (DMEM/10% FCS (Biowest, Cat. No. 12362; Biochrom, Cat. No. S0415)) in 12 well plates. 24 h post seeding the medium of the cells was removed and VSV-G pseudotyped lentiviral vector particles encoding for CD19-CAR or CD318-CAR and LNGFR were added in 500 μl DMEM w/o FCS at an MOI of 30 to the cells. 24 h post transduction the medium containing excess LV was removed and 2 ml fresh cultivation medium was added. LNGFR expression of the cells was analyzed one week post transduction by staining for the LNGFR protein (α-LNGFR-APC, Miltenyi Biotec, 130-112-602) by flow cytometry. The bulk population was used two weeks post transduction for generation of lentiviral vector particles (Example 2).

Example 4: Binding of Lentiviral Vector Particles to Unstimulated PBMC

PBMC were isolated from Buffy coat and WBC number was determined using Sysmex XP-300™ automated hematology analyzer. 2.5E5 WBC were resuspended in 150 μl TexMACS Medium (Miltenyi Biotec, Cat. No. 130-097-196) (w/o supplements) and seeded in 96 well plates. Lentiviral vector particles encoding for and displaying CAR were diluted in 50 μl TexMACS (w/o supplements) and added at a MOI of 40 (FIG. 2A, 2B, 4) or an MOI of 200 (FIG. 3) to the cells. After binding for 1 h at 4° C., excess LV was removed by one washing step and staining was performed with 7AAD (Miltenyi Biotec, cat. No. 130-111-568), CD3-APC (Miltenyi Biotec, cat. No. 130-113-135), CD3-Vioblue (Miltenyi Biotec, cat. No. 130-114,519), CD4-Vioblue (Miltenyi Biotec, cat. No. 130-114-534), CD8-APC-Vio (Miltenyi Biotec, cat. No. 130-110-681), CD14-Viogreen (Miltenyi Biotec, cat. No. 130-110-525), CD16-PE (Miltenyi Biotec, cat. No. 130-113-393), CD56-PE (Miltenyi Biotec, cat. No. 130-113-312), CD19-PE-Vio (Miltenyi Biotec, cat. No. 130-113-647), LNGFR-FITC (Miltenyi Biotec, cat. No. 130-112-605) and LNGFR-APC (Miltenyi Biotec, cat. No. 130-112-602). Binding of lentiviral vector particles was evaluated by flow cytometry by quantification of LNGFR or GFP positive cells of the different cell types which were identified by specific surface markers namely T cells (CD3+, CD56−), B cells (CD3−, CD19+), NK cells (CD3−CD14−CD56/CD16+) and monocytes (CD3−CD14+).

Figure 2B:
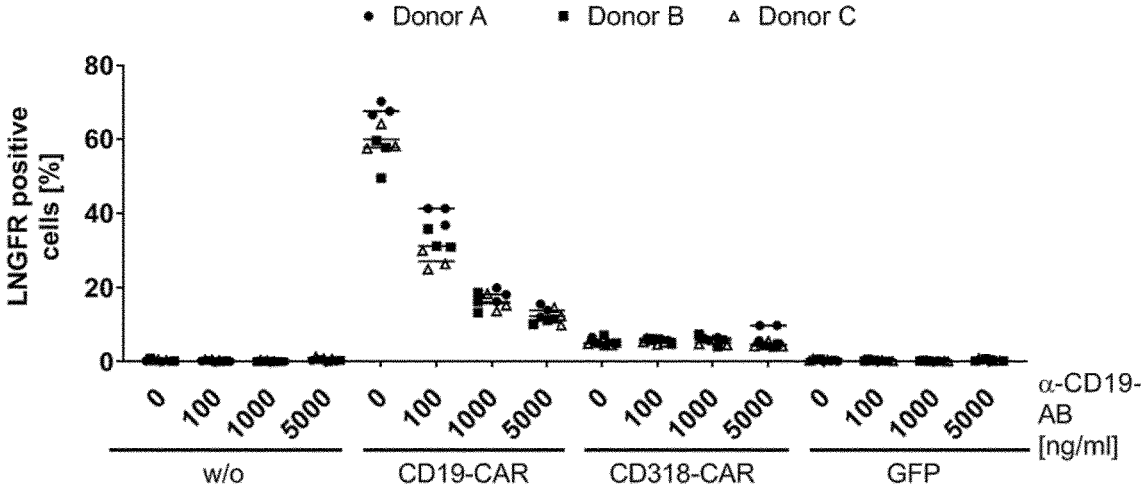

Example 5: Blocking the Binding of Lentiviral Vector Particles Displaying CARs to B Cells PBMC were isolated from Buffy coat and the WBC number was determined using Sysmex XP-300™ automated hematology analyzer. 2.5E5 WBC were resuspended in 150 μl TexMACS Medium (Miltenyi Biotec, Cat. No. 130-097-196) (w/o supplements) and seeded in 96 well plates. A α-CD19-AB (Clone: LT19, Miltenyi Biotec) was added in different concentrations (0 ng/ml, 100 ng/ml, 1000 ng/ml and 5000 ng/ml) to the cells. After incubating for 30 min, lentiviral vector particles displaying CAR specific for CD19 or CD318 were added for 1 h at 4° C. Excess LV was removed by one washing step and LNGFR staining was performed to detect bound lentiviral vectors particles and quantify the blocking efficiency of the CD19 specific antibody to inhibit binding of lentiviral particles displaying CD19-CAR or CD318-CAR to the B cells. (FIG. 2B)

Example 6: Isolation and Transduction of T Cells

Primary T cells of 2 donors were isolated from PBMC using the PAN T cell isolation Kit (Miltenyi Biotec, 130-096-535) and cultivated in TexMACS medium (Miltenyi Biotec, 130-097-196) with IL7 (Miltenyi Biotec, 170-076-111) IL15 (Miltenyi Biotec, 170-076-114) and Transact (Miltenyi Biotec, 130-111-160) over night at 37° C. Half of the samples were treated with the integration inhibitor Raltegravir (Sigma Aldrich, cat. No. CDS023737-25MG). Lentiviral vector particles encoding for GFP but displaying CD19-CAR, CD318-CAR or no CAR on the surface were diluted in 50 μl TexMACS per well and added to the cells.

3 days post activation, the medium of the cell was exchanged with fresh TexMACS with IL7 and IL15. Transduction efficiency of the T cell population (CD3+) was analyzed 4 days post transduction using flow cytometry quantifying the GFP positive cells. (FIG. 5A)

Example 7: Transduction of a Sample Containing Malignant B Cells and PBMC

Malignant B cells of three B-ALL patients were isolated by Ficoll from leukapheresis samples. Malignant B cells were characterized by evaluation of surface markers using flow cytometry: CD45-Vioblue (Miltenyi Biotec, cat. No. 130-110-637), IgKappa-Viogreen (Miltenyi Biotec, cat. No. 130-122-224), IgLambda-APC-Vio (Miltenyi Biotec, cat. No. 130-105-106), CD5-PE (Miltenyi Biotec, cat. No. 130-110-991), CD10-APC (Miltenyi Biotec, cat. No. 130-114-503), CD20-PE-Vio (Miltenyi Biotec, cat. No. 130-111-340), CD34-PE (Miltenyi Biotec, cat. No. 130-120-515) and CD19-FITC (Miltenyi Biotec, cat. No. 130-113-645). The applied malignant B cells were positive for CD19+, CD5/10+, CD34+ but negative for CD20–. PBMC of healthy donors were isolated from Buffy Coat using Ficoll and cell numbers were determined using Sysmex XP-300™ automated hematology analyzer. 2.8E5 white blood cells (WBC) and 1.2E5 malignant B cells were seeded in 150 µl TexMACS medium w/o supplements into 96 well plates (Miltenyi Biotec, Cat. No. 130-097-196) (FIG. 5B). Besides the coculture of malignant B cells and PBMC, a coculture of activated T cells and malignant cells was setup. Therefore, T cells of two healthy donors were isolated from PBMC using the PAN T cell isolation kit and cell numbers were determined using a Neubauer Chamber and 2.8E5 malignant B cells and 1.2E5 activated T cells were seeded in 150 µl TexMACS medium w/o supplements into 96 well plates (Miltenyi Biotec, Cat. No. 130-097-196) (FIG. 5C). For both cocultures, half of the samples were treated with the integration inhibitor Raltegravir (Sigma Aldrich, cat. No. CDS023737-25MG) at a concentration of 1 µM. Lentiviral vector particles encoding for GFP but displaying CD19, CD318 or no CAR were diluted in 50 µl TexMACS per well and added to the cells. After an incubation time of 1.5 h at 37° C. excess lentiviral vector was removed by extensive washing. For the coculture of PBMC with malignant cells the cells were resuspended in 200 µl RPMI medium supplemented with 2 mM stable Glutamin (Biowest, Cat. No. L0501-500; Lonza, Cat. No. 882027-12), 20% FCS (Hyclone, GE Healthcare, cat. No. SH30080.03), 60 ng/ml IL3 (Miltenyi Biotec, cat. No. 60 ng/ml), 300 ng/ml SCF (Miltenyi Biotec, cat. No. 170-076-133) and 300 ng/ml Flt-3 (Miltenyi Biotec, cat. No. 170-076-132) (FIG. 5B). For the coculture of activated T cells with malignant B cells, the cells were resuspended in 200 µl TexMACS with IL7 and IL15 (FIG. 5C) and further cultivated at 37° C. For both types of coculture the transduction efficiency on the (malignant) B cell population (CD3–, CD20–, CD19+) was analyzed 4 days post transduction using flow cytometry quantifying the GFP positive cells. (FIG. 5B, C)

Example 8: Generation of Patient Derived Adapter-CAR T Cells Directly in a Sample Comprising T Cells and Malignant Cells A sample containing T cells and malignant cells is automatically prepared from a leukapheresis of B-ALL patient in the CliniMACS Prodigy. 1E8 white-blood cells containing 30% malignant B cells are seeded in TexMACS containing IL7/IL15 at a density of 1E6 cells/ml. The T cells within the sample are activated for 24 h at 37° C. by adding CD3/CD28 specific Transact. VSV-G pseudotyped lentiviral vector particles encoding AdapterCAR are added to the sample at a MOI of 5. One day post activation the medium of the cells is removed and exchanged with fresh TexMACS to remove the Transact and excess lentiviral vector particles. The cells are further expanded for 3-5 days. Additional washing steps ensure sufficient removal of residual lentiviral vector particles. Cellular composition, transduction efficiency on T and malignant cells and the ratio of malignant cells is evaluated by flow cytometry 5 days post transduction and on the day of harvest. After harvest, the sample comprising AdapterCAR T cells and malignant cells is combined with tagged adapter at a concentration of 100 ng/ml. The adapter concentration is adjusted to the adapter format and the specificity of the adapter molecule. Specific lysis of the tumor cells will be evaluated by quantification of the remaining viable tumor cells by flow cytometry.

REFERENCES

Bender, R. R. et al. Receptor-Targeted Nipah Virus Glycoproteins Improve Cell-Type Selective Gene Delivery and Reveal a Preference for Membrane-Proximal Cell Attachment. *PLoS Pathog.* 12, (2016).

Drent, E. et al. Feasibility of controlling CD38-CAR T cell activity with a Tet-on inducible CAR design. *PLoS One* 13, (2018).

Holic, N. et al. Influence of mildly acidic pH conditions on the production of lentiviral and retroviral vectors. *Hum. Gene Ther. Clin. Dev.* 25, 178-185 (2014).

Jamali, A. et al. Highly Efficient and Selective CAR-Gene Transfer Using CD4- and CD8-Targeted Lentiviral Vectors. *Mol. Ther.-Methods Clin. Dev.* 13, 371-379 (2019).

Ruella, M. et al. Induction of resistance to chimeric antigen receptor T cell therapy by transduction of a single leukemic B cell. *Nat. Med.* 24, 1499-1503 (2018).

Sakemura, R. et al. A Novel Strategy of Switching on/Off CD19CAR Expression Under Tetracycline-Based System. *Blood* 126, 4424 (2015).

The invention claimed is:

1. An improved method for preparing a therapeutic population of T cells to treat a subject who has circulating malignant cells,
   wherein the method comprises contacting T cells from the subject with lentiviral vector particles that encode a chimeric antigen receptor (CAR) specific for a tumor antigen on the malignant cells, thereby transducing the T cells to express the CAR;
   wherein the improvement comprises:
   (a) using lentiviral vector particles that are pseudotyped with an envelope protein that binds T cells, and that encode a CAR that binds the tag of a tagged polypeptide instead of said tumor antigen;
   (b) contacting the T cells with said pseudotyped lentiviral vector particles in a mixed cell population from the subject that also contains circulating malignant cells, whereupon the pseudotyped lentiviral vector particles selectively transduce the T cells in preference to the circulating malignant cells in the mixed cell population; wherein the T cells obtained thereby specifically bind said tagged polypeptide, and are effective in treating the subject when administered to the subject in combination with said tagged polypeptide.

2. The method according to claim 1, wherein said malignant cells are circulating tumor cells (CTCs), malignant B cells, malignant B cell subsets, malignant B cell progenitors, malignant NK cells, malignant stem cells, malignant myeloid cells, malignant myeloid subsets or malignant myeloid progenitors.

3. The method according to claim 1, wherein said CAR binds to a tag selected from the group consisting of dextran, biotin, fluorescein isothiocyanate (FITC), phycoerythrin (PE), and a peptide.

4. The method according to claim 1, wherein said T cells of said mixed cell population from the subject is a population comprising activated T cells.

5. The method according to claim 1, wherein said circulating malignant cells are malignant B cells, malignant B cell subsets or malignant B cell progenitors, and wherein said tumor antigen is selected from the group consisting of CD10, CD19, CD20, CD22, CD24, CD33, CD34, and CD79a.

6. The method of claim 1, wherein said envelope protein is selected from the group consisting of BaEV env, VSV-G, RD114-TR, GALV-TR, MV-H/F, NiV-G/F, and Ampho-MLV env.

7. The method of claim 1, wherein said pseudotyped lentiviral vector particles are pseudotyped with vesicular stomatitis virus G protein (VSV-G), which selectively binds to LDL receptors (LDLR) on the T cells in the mixed cell population from the subject.

8. The method of claim 1, wherein the mixed cell population is a sample of whole blood, a leukapheresis, a buffy coat, or peripheral blood mononuclear cells (PBMC).

* * * * *